United States Patent
Sidransky

(10) Patent No.: US 7,279,312 B2
(45) Date of Patent: Oct. 9, 2007

(54) NUCLEIC ACID MUTATION DETECTION BY ANALYSIS OF SALIVA

(75) Inventor: David Sidransky, Baltimore, MD (US)

(73) Assignee: The Johns Hopkins University School of Medicine, Baltimore, MD (US)

(*) Notice: Subject to any disclaimer, the term of this patent is extended or adjusted under 35 U.S.C. 154(b) by 206 days.

(21) Appl. No.: 10/754,478

(22) Filed: Jan. 9, 2004

(65) Prior Publication Data

US 2005/0009040 A1 Jan. 13, 2005

Related U.S. Application Data

(63) Continuation of application No. 09/863,806, filed on May 22, 2001, now abandoned, which is a continuation of application No. 09/038,637, filed on Mar. 10, 1998, now Pat. No. 6,235,470, which is a continuation-in-part of application No. 08/579,223, filed on Dec. 28, 1995, now Pat. No. 5,726,019, which is a continuation of application No. 08/152,313, filed on Nov. 12, 1993, now Pat. No. 5,561,041.

(51) Int. Cl.
*C12P 19/34* (2006.01)

(52) U.S. Cl. .................................................. 435/91.2

(58) Field of Classification Search ..................... None
See application file for complete search history.

(56) References Cited

U.S. PATENT DOCUMENTS 6,150,100 A * 11/2000 Ruschoff et al. ............... 435/6

FOREIGN PATENT DOCUMENTS

EP 0 520 794 A 12/1992
WO WO93/20235 10/1993
WO WO93/22456 11/1993

OTHER PUBLICATIONS

Hampton et al., Simultaneous assessment of loss of heterozygosity at multiple microsatellite loci using semi-automated fluorescence-based detection: Subregional mapping of chromosome 4 in cervical carcinoma, 1996, Proc. Natl. Acad. Sci. USA vol. 93, pp. 6704-6709.*
Fearon, Eric R., et al., "Identification of a Chromosome 18q Gene That Is Altered in Colorectal Cancers", *Science, American Association for the Advancement of Science*, vol. 247(5), pp. 49-56, (1990).
Goyette, Michelle et al., "Progression of Colorectal Cancer Is Associated with Multiple Tumor Suppressor Gene Defects but Inhibition of Tumorigenicity Is Accomplished by Correction of Any Single Defect via Chromosome Transfer", *Molecular and Cellular Biology*, vol. 12(3), pp. 1387-1395, (Mar. 1992).
Kinzler, K.W. et al., "Identification of a Gene Located at Chromosome 5q21 That is Mutated in Colorectal Cancers", *Science*, vol. 251(15), pp. 1366-1370 (1991).
Miyoshi, Yasuo et al., "Germ-line mutations of the APC gene in 53 familial adenomatous polyposis patients", *Proc. Natl. Acad. Sci.*, vol. 89, pp. 4452-4456 (1992).
Nishisho, I. et al., "Mutations of Chromosome 5q21 Genes in FAP and Colorectal Cancer Patients", *Science*, vol. 253(9), pp. 665-669, (1991).
Powell, Steven M., "Molecular Diagnosis of Familial Adenomatous Polyposis", *New England Journal of Medicine*, vol. 329(27), pp. 1982-1987, (1993).

* cited by examiner

*Primary Examiner*—Kenneth R. Horlick
*Assistant Examiner*—Mark Staples
(74) *Attorney, Agent, or Firm*—DLA Piper US LLP

(57) ABSTRACT

Methods for detection of a cell proliferative disorder, such as cancer, are provided utilizing analysis of target mutant nucleic acids in saliva specimens. The presence of the target mutant nucleic acids is indicative of a neoplastic disorder of the lung or the head and neck.

10 Claims, 3 Drawing Sheets

SEQUENCE LISTING (1) GENERAL INFORMATION:

(iii) NUMBER OF SEQUENCES: 195

(2) INFORMATION FOR SEQ ID NO: 1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO: 1:

CTTGTGTCCC GGCGTCTG                  18

(2) INFORMATION FOR SEQ ID NO: 2:

(i) SEQUENCE CHARACTERISTICS:
      (A) LENGTH: 19 base pairs (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 2:

CAGCCCAGCA GGACCAGTA                                                19

(2) INFORMATION FOR SEQ ID NO: 3:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 3:

TGGTAACAGT GGAATACTGA C                                             21

(2) INFORMATION FOR SEQ ID NO: 4:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 4:

ACTGATGCAA AAATCCTCAA C                                             21

(2) INFORMATION FOR SEQ ID NO: 5:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 5:

GATGGGCAAA CTGCAGGCCT GGGAAG                                        26

(2) INFORMATION FOR SEQ ID NO: 6:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 6:

GCTACAAGGA CCCTTCGAGC CCCGTTC                                       27

(2) INFORMATION FOR SEQ ID NO: 7:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 7:

GATGGTGATG TGTTGAGACT GGTG                                          24

(2) INFORMATION FOR SEQ ID NO: 8:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 8:

GAGCATTTCC CCACCCACTG GAGG                                          24

(2) INFORMATION FOR SEQ ID NO: 9:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 9:

GTTCTGGATC ACTTCGCGGA                                               20

(2) INFORMATION FOR SEQ ID NO: 10:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 10:

TGAGGATGGT TCTCCCCAAG                                               20

(2) INFORMATION FOR SEQ ID NO: 11:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 11:

AGTGGTGAAT TAGGGGTGTT                                               20

(2) INFORMATION FOR SEQ ID NO: 12:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 12:

| | |
|---|---|
| CTGCCATCTT GTGGAATCAT | 20 |

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 13:

| | |
|---|---|
| CTGTGAGTTC AAAACCTATG G | 21 |

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 14:

| | |
|---|---|
| GTGTCAGAGG ATCTGAGAAG | 20 |

(2) INFORMATION FOR SEQ ID NO: 15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 15:

| | |
|---|---|
| GCACGCTCTG GAACAGATTC TGGA | 24 |

(2) INFORMATION FOR SEQ ID NO: 16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 16:

| | |
|---|---|
| ATGAGGAACA GCAACCTTCA CAGC | 24 |

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 17:

| | |
|---|---|
| TCACTCTTGT CGCCCAGATT | 20 |

(2) INFORMATION FOR SEQ ID NO: 18:

```
        (i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 18:

TATAGCGGTA GGGGAGATGT                                              20

(2) INFORMATION FOR SEQ ID NO: 19:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 19:

TGCAAGGAGA AAGAGAGACT GA                                           22

(2) INFORMATION FOR SEQ ID NO: 20:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 20:

AACAGGACCA CAGGCTCCTA                                              20

(2) INFORMATION FOR SEQ ID NO: 21:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 21:

TCTCTTTCTT TCCTTGACAG GGTC                                         24

(2) INFORMATION FOR SEQ ID NO: 22:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 22:

CAGTGTGGTC CCAAATTTGA AATGG                                        25

(2) INFORMATION FOR SEQ ID NO: 23:

(i) SEQUENCE CHARACTERISTICS:
            (A) LENGTH: 19 base pairs
            (B) TYPE: nucleic acid
```

-continued (C) STRANDEDNESS: single
        (D) TOPOLOGY: linear (ii) MOLECULE TYPE: Genomic DNA (xi) SEQUENCE DESCRIPTION: SEQ ID NO: 23:

GTGCTGACTA GGGCAGCTT                                             19

(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 24:

TGTGACCTGC ACTCGGAAGC                                            20

(2) INFORMATION FOR SEQ ID NO: 25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 25:

CCTTTCCTTC CTTCCTTCC                                             19

(2) INFORMATION FOR SEQ ID NO: 26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 26:

CACAGTCAGG TCAGGCTATC AG                                         22

(2) INFORMATION FOR SEQ ID NO: 27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 27:

TTTTTGAGAT AGAGTCTCAC TGTG                                       24

(2) INFORMATION FOR SEQ ID NO: 28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 28:

CCACAGTCTA AGCCAGTCTG A                                   21

(2) INFORMATION FOR SEQ ID NO: 29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 29:

GAATTTTGCT CTTGTTGCCC AG                                  22

(2) INFORMATION FOR SEQ ID NO: 30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 30:

AGACTGAAGT CAATGAACAA CAAC                                24

(2) INFORMATION FOR SEQ ID NO: 31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 31:

GGCTGTGAAC ATGGCCTAGG TC                                  22

(2) INFORMATION FOR SEQ ID NO: 32:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 32:

TTGGGGTGGT GCCAATGGAT GTC                                 23

(2) INFORMATION FOR SEQ ID NO: 33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 33:

CAGACGCCGG GACACAAG                                       18

(2) INFORMATION FOR SEQ ID NO: 34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 34:

TACTGGTCCT GCTGGGCTG                                                 19

(2) INFORMATION FOR SEQ ID NO: 35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 35:

GTCAGTATTA CCCTGTTACC A                                          21

(2) INFORMATION FOR SEQ ID NO: 36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 36:

GTTGAGGATT TTTGCATCAG T                                          21

(2) INFORMATION FOR SEQ ID NO: 37:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 37:

CTTCCCAGGC CTGCAGTTTG CCCATC                                  26

(2) INFORMATION FOR SEQ ID NO: 38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 38:

GAACGGGGCT CGAAGGGTCC TTGTAGC                                27

(2) INFORMATION FOR SEQ ID NO: 39:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO: 39:

CACCAGTCTC AACACATCAC CATC                                    24

(2) INFORMATION FOR SEQ ID NO: 40:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO: 40:

CCTCCAGTGG GTGGGGAAAT GCTC                                    24

(2) INFORMATION FOR SEQ ID NO: 41:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO: 41:

TCCGCGAAGT GATCCAGAAC                                         20

(2) INFORMATION FOR SEQ ID NO: 42:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO: 42:

CTTGGGGAGA ACCATCCTCA                                         20

(2) INFORMATION FOR SEQ ID NO: 43:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO: 43:

AACACCCCTA ATTCACCACT                                         20

(2) INFORMATION FOR SEQ ID NO: 44:

(i) SEQUENCE CHARACTERISTICS:
          (A) LENGTH: 20 base pairs
          (B) TYPE: nucleic acid
          (C) STRANDEDNESS: single (D) TOPOLOGY: linear (ii) MOLECULE TYPE: Genomic DNA (xi) SEQUENCE DESCRIPTION: SEQ ID NO: 44:

ATGATTCCAC AAGATGGCAG                                                         20

(2) INFORMATION FOR SEQ ID NO: 45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 45:

CCATAGGTTT TGAACTCACA G                                                       21

(2) INFORMATION FOR SEQ ID NO: 46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 46:

CTTCTCAGAT CCTCTGACAC                                                         20

(2) INFORMATION FOR SEQ ID NO: 47:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 47:

TCCAGAATCT GTTCCAGAGC GTGC                                                    24

(2) INFORMATION FOR SEQ ID NO: 48:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 48:

GCTGTGAAGG TTGCTGTTCC TCAT                                                    24

(2) INFORMATION FOR SEQ ID NO: 49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 49:

AATCTGGGCG ACAAGAGTGA                                           20

(2) INFORMATION FOR SEQ ID NO: 50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 50:

ACATCTCCCC TACCGCTATA                                           20

(2) INFORMATION FOR SEQ ID NO: 51:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 51:

TCAGTCTCTC TTTCTCCTTG CA                                        22

(2) INFORMATION FOR SEQ ID NO: 52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 52:

TAGGAGCCTG TGGTCCTGTT                                           20

(2) INFORMATION FOR SEQ ID NO: 53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 53:

GACCCTGTCA AGGAAAGAAA GAGA                                      24

(2) INFORMATION FOR SEQ ID NO: 54:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 54:

CCATTTCAAA TTTGGGACCA CACTG                                     25

(2) INFORMATION FOR SEQ ID NO: 55:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 55:

AAGCTGCCCT AGTCAGCAC                                  19

(2) INFORMATION FOR SEQ ID NO: 56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 56:

GCTTCCGAGT GCAGGTCACA                                20

(2) INFORMATION FOR SEQ ID NO: 57:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 57:

GGAAGGAAGG AAGGAAAGG                                  19

(2) INFORMATION FOR SEQ ID NO: 58:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 58:

CTGATAGCCT GACCTGACTG TG                              22

(2) INFORMATION FOR SEQ ID NO: 59:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 59:

CACAGTGAGA CTCTATCTCA AAAA                            24

(2) INFORMATION FOR SEQ ID NO: 60:

(i) SEQUENCE CHARACTERISTICS:

```
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 60:

TCAGACTGGC TTAGACTGTG G                                              21

(2) INFORMATION FOR SEQ ID NO: 61:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 61:

CTGGGCAACA AGAGCAAAAT TC                                             22

(2) INFORMATION FOR SEQ ID NO: 62:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 62:

GTTGTTGTTC ATTGACTTCA GTCT                                           24

(2) INFORMATION FOR SEQ ID NO: 63:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 63:

GACCTAGGCC ATGTTCACAG CC                                             22

(2) INFORMATION FOR SEQ ID NO: 64:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 64:

GACATCCATT GGCACCACCC CAA                                            23

(2) INFORMATION FOR SEQ ID NO: 65:

(i) SEQUENCE CHARACTERISTICS:
        (A) LENGTH: 22 base pairs
        (B) TYPE: nucleic acid
        (C) STRANDEDNESS: single
        (D) TOPOLOGY: linear
```

-continued (ii) MOLECULE TYPE: Genomic DNA (xi) SEQUENCE DESCRIPTION: SEQ ID NO: 65:

GATCCACCAA AGCATATTAT GA                                        22

(2) INFORMATION FOR SEQ ID NO: 66:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 66:

TTAAGCATCT TGAATTTTGC CT                                        22

(2) INFORMATION FOR SEQ ID NO: 67:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 67:

GTTTCTCCAG AACAGAACCA ATAAG                                     25

(2) INFORMATION FOR SEQ ID NO: 68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 68:

TAACCATGTA AGCCAGTCCC                                           20

(2) INFORMATION FOR SEQ ID NO: 69:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 69:

GGCTGAGACA TAAGACTCAC TTGAAC                                    26

(2) INFORMATION FOR SEQ ID NO: 70:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 70:

```
TCCATGATGG CTAATGATAC TGAG                                              24
```

(2) INFORMATION FOR SEQ ID NO: 71:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 71:

```
ACAGAGCAAG GTTGCCCAG                                                    19
```

(2) INFORMATION FOR SEQ ID NO: 72:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 72:

```
TCCACTCAGC ACCAACAGT                                                    19
```

(2) INFORMATION FOR SEQ ID NO: 73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 73:

```
GCAATGACCA GTTAAGGTTC                                                   20
```

(2) INFORMATION FOR SEQ ID NO: 74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 74:

```
AATTCCCACA ACAAATCTCC                                                   20
```

(2) INFORMATION FOR SEQ ID NO: 75:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 75:

```
TGCGCGTTAA GTTAATTGGT T                                                 21
```

(2) INFORMATION FOR SEQ ID NO: 76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 76:

GTAAGGTGGA AACCCCCACT                                           20

(2) INFORMATION FOR SEQ ID NO: 77:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 77:

AGCTAAGTGA ACCTCATCTC TGTCT                                     25

(2) INFORMATION FOR SEQ ID NO: 78:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 78:

ACCCTAGCAC TGATGGTATA GTCT                                      24

(2) INFORMATION FOR SEQ ID NO: 79:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 79:

GCCATTATTG ACTCTGGAAA AGAC                                      24

(2) INFORMATION FOR SEQ ID NO: 80:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 80:

CAGGCTCTCA AAATATGAAC AAAAT                                     25

(2) INFORMATION FOR SEQ ID NO: 81:

(i) SEQUENCE CHARACTERISTICS:
        (A) LENGTH: 19 base pairs (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 81:

CAGCTGCCCT AGTCAGCAC                                                    19

(2) INFORMATION FOR SEQ ID NO: 82:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 82:

AGGCAATAGA GACCCTGTG                                                    19

(2) INFORMATION FOR SEQ ID NO: 83:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 83:

AAGGAAGGAA GGAAGGAAAG G                                                 21

(2) INFORMATION FOR SEQ ID NO: 84:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 84:

GATGATGAAT TGTTACTGAG AG                                                22

(2) INFORMATION FOR SEQ ID NO: 85:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 85:

CCAGTGACTA CTTTGATTCG                                                   20

(2) INFORMATION FOR SEQ ID NO: 86:

(i) SEQUENCE CHARACTERISTICS:
        (A) LENGTH: 22 base pairs
        (B) TYPE: nucleic acid
        (C) STRANDEDNESS: single
        (D) TOPOLOGY: linear -continued (ii) MOLECULE TYPE: Genomic DNA (xi) SEQUENCE DESCRIPTION: SEQ ID NO: 86:

TGGCCTTTCA CATGGATGTG AA                                                    22

(2) INFORMATION FOR SEQ ID NO: 87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 87:

GGGCAACAAG GAGAGACTCT                                                      20

(2) INFORMATION FOR SEQ ID NO: 88:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 88:

AAAAAAGGAC CTGCCTTTAT CC                                                   22

(2) INFORMATION FOR SEQ ID NO: 89:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 89:

TTGCACTCCA CTCTGGGCA                                                      19

(2) INFORMATION FOR SEQ ID NO: 90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 90:

TTGCCTTGGC TTTCTGTTGG                                                    20

(2) INFORMATION FOR SEQ ID NO: 91:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 91:

```
TTTGTTGTTG TTCATTGACT TCAGTCT                                        27
```

(2) INFORMATION FOR SEQ ID NO: 92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 92:

```
ATTTACCTAC CTGTTCATCC                                                20
```

(2) INFORMATION FOR SEQ ID NO: 93:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 93:

```
GAGCCATGTT CATGCCCACT G                                              21
```

(2) INFORMATION FOR SEQ ID NO: 94:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 94:

```
CAAACCCGAC TAACCAGCAA C                                              21
```

(2) INFORMATION FOR SEQ ID NO: 95:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 95:

```
GCCTTGATCA CACCACTACA                                                20
```

(2) INFORMATION FOR SEQ ID NO: 96:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 96:

```
GTGGTCACTA AAGTTTCTGC T                                              21
```

(2) INFORMATION FOR SEQ ID NO: 97:

```
    (i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 97:

ATTACAGTGT GAGACCCTG                                                        19

(2) INFORMATION FOR SEQ ID NO: 98:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 98:

GAGTATCCAG AGAGCTATTA                                                       20

(2) INFORMATION FOR SEQ ID NO: 99:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 99:

TTGCTCCAAC CAGGAGGCA                                                        19

(2) INFORMATION FOR SEQ ID NO: 100:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 100:

GAACCAAGGA AGTTGTTCAA C                                                     21

(2) INFORMATION FOR SEQ ID NO: 101:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 101:

GCAGTGAGTT CATATGGCTA                                                       20

(2) INFORMATION FOR SEQ ID NO: 102:

(i) SEQUENCE CHARACTERISTICS:
        (A) LENGTH: 20 base pairs
        (B) TYPE: nucleic acid
```

```
        (C) STRANDEDNESS: single
        (D) TOPOLOGY: linear (ii) MOLECULE TYPE: Genomic DNA (xi) SEQUENCE DESCRIPTION: SEQ ID NO: 102:

GTTTCTCTGT TCAGCACTTC                                               20

(2) INFORMATION FOR SEQ ID NO: 103:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 103:

TGGCGAGACT CCATCAAAG                                                19

(2) INFORMATION FOR SEQ ID NO: 104:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 104:

CCTTTTAAGC TGCAACAATT TC                                            22

(2) INFORMATION FOR SEQ ID NO: 105:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 105:

CAGGTTGCTA ACCACCCTGT                                               20

(2) INFORMATION FOR SEQ ID NO: 106:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 106:

GTGCACACTT GGACAGCATT                                               20

(2) INFORMATION FOR SEQ ID NO: 107:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA
```

(xi) SEQUENCE DESCRIPTION: SEQ ID NO: 107:

CTGACTCCAG AGCCTGGG                                              18

(2) INFORMATION FOR SEQ ID NO: 108:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 108:

GGTTGAATGT GGCGTGTTC                                             19

(2) INFORMATION FOR SEQ ID NO: 109:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 109:

ACAATGAACA TCCATATACC C                                          21

(2) INFORMATION FOR SEQ ID NO: 110:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 110:

ACCATGATTT GTCAACTCCT A                                          21

(2) INFORMATION FOR SEQ ID NO: 111:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 111:

GCATCTTGTT AGGGCAGCC                                             19

(2) INFORMATION FOR SEQ ID NO: 112:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 112:

CCTGCAGATT TTTGATTTAC C                                          21

(2) INFORMATION FOR SEQ ID NO: 113:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 113:

GACCCCACAG CCTATTCAGA                                        20

(2) INFORMATION FOR SEQ ID NO: 114:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 114:

TTGACTGCTG AACGGCTGCA                                        20

(2) INFORMATION FOR SEQ ID NO: 115:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 115:

GAAGATTGCA GAGCTTTCTG CCAC                                  24

(2) INFORMATION FOR SEQ ID NO: 116:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 116:

GTAAGTTCTC CTGGAGCAAG CTTC                                  24

(2) INFORMATION FOR SEQ ID NO: 117:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 117:

GAGGCTACAG TAAGCCAAGA GTGC                                  24

(2) INFORMATION FOR SEQ ID NO: 118:

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 118:

GCCTTCCAAA ATGCAAGGAT TACA                                              24

(2) INFORMATION FOR SEQ ID NO: 119:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 119:

GTTGAACAGG AGCAGTGAGA G                                                 21

(2) INFORMATION FOR SEQ ID NO: 120:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 120:

AGAGAAAGAG AGACAGAAAG AGAGA                                             25

(2) INFORMATION FOR SEQ ID NO: 121:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 121:

GCACCAATGC TCCAGAAATG                                                   20

(2) INFORMATION FOR SEQ ID NO: 122:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 122:

TCATGGTGCC ATGATAGGAG                                                   20

(2) INFORMATION FOR SEQ ID NO: 123:

(i) SEQUENCE CHARACTERISTICS:
        (A) LENGTH: 22 base pairs
        (B) TYPE: nucleic acid
        (C) STRANDEDNESS: single
```

(D) TOPOLOGY: linear (ii) MOLECULE TYPE: Genomic DNA (xi) SEQUENCE DESCRIPTION: SEQ ID NO: 123:

TAGGTAGTAA ACTTCATACA CG                                        22

(2) INFORMATION FOR SEQ ID NO: 124:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 124:

CTCATCTGCC TATATCACAG C                                         21

(2) INFORMATION FOR SEQ ID NO: 125:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 125:

TGATCTTCAA AGAGAGTTCC G                                         21

(2) INFORMATION FOR SEQ ID NO: 126:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 126:

AGTTCGATAG CACTCGCCGT                                           20

(2) INFORMATION FOR SEQ ID NO: 127:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 127:

TGGCGCTGAT GCTCCACATT C                                         21

(2) INFORMATION FOR SEQ ID NO: 128:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 128:

CTGGCTGACA GATAAAGCAC T                                      21

(2) INFORMATION FOR SEQ ID NO: 129:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 129:

GCAGTGAGCT GAGATAATGC                                        20

(2) INFORMATION FOR SEQ ID NO: 130:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 130:

TCACTAGCAG ATGCGATAAT G                                      21

(2) INFORMATION FOR SEQ ID NO: 131:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 131:

GGATATAGCT GGCAATGGC                                         19

(2) INFORMATION FOR SEQ ID NO: 132:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 132:

TCGGAATGCC TACTTCCCAG                                        20

(2) INFORMATION FOR SEQ ID NO: 133:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 133:

GTGAGAGTTC CTTCTGGC                                          18

(2) INFORMATION FOR SEQ ID NO: 134:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 134:

ACTCCAGTAC AAGACTCTG                                            19

(2) INFORMATION FOR SEQ ID NO: 135:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 135:

AGCCTGGGTG ACAAAGCAAG                                         20

(2) INFORMATION FOR SEQ ID NO: 136:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 136:

GCTCCACACC ACACACATG                                            19

(2) INFORMATION FOR SEQ ID NO: 137:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 137:

AGATCGCGCC ATTGTACTC                                            19

(2) INFORMATION FOR SEQ ID NO: 138:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 138:

AGCTCAGGGC ATTCTGTGAA                                         20

(2) INFORMATION FOR SEQ ID NO: 139:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 139:

GGACTGCATC TTAGGTGCTA                                           20

(2) INFORMATION FOR SEQ ID NO: 140:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 140:

CACCAATGCA GTCTAGCCT                                            19

(2) INFORMATION FOR SEQ ID NO: 141:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 141:

ACGCTGGGCT AATTCTTG                                             18

(2) INFORMATION FOR SEQ ID NO: 142:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 142:

AGAGGCCAGG AGTTTGAG                                             18

(2) INFORMATION FOR SEQ ID NO: 143:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 143:

TTGCACCACT ATACTCCAGC                                           20

(2) INFORMATION FOR SEQ ID NO: 144:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 144:

TCAGTTTAAG GTTCTCACCT G                                             21

(2) INFORMATION FOR SEQ ID NO: 145:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 145:

TCCTTTGTTG CAGATTTCTT C                                             21

(2) INFORMATION FOR SEQ ID NO: 146:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 146:

TGCATACCTG TACTACTTCA G                                             21

(2) INFORMATION FOR SEQ ID NO: 147:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 147:

AGGCAATAGA GACCCTGTG                                                19

(2) INFORMATION FOR SEQ ID NO: 148:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 148:

GATGATGAAT TGTTACTGAG AG                                            22

(2) INFORMATION FOR SEQ ID NO: 149:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 149:

AAGGGCTGTC ATGTAGCAAG                    20

(2) INFORMATION FOR SEQ ID NO: 150:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 150:

CAATCCAGGG AAGTTTCCAT                    20

(2) INFORMATION FOR SEQ ID NO: 151:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 151:

GTGAGAGTTC CTTCTGGC                      18

(2) INFORMATION FOR SEQ ID NO: 152:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 152:

ACTCCAGTAC AAGACTCTG                     19

(2) INFORMATION FOR SEQ ID NO: 153:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 153:

TGGCAGTGCA AGACTCTTT                     19

(2) INFORMATION FOR SEQ ID NO: 154:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 154:

TGAGGATTCC AGCAATGCT                     19

(2) INFORMATION FOR SEQ ID NO: 155:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 155:

TCACCACTGC ACTCCAGCCT                                            20

(2) INFORMATION FOR SEQ ID NO: 156:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 156:

GGACTCACCT TATGCCATGT                                            20

(2) INFORMATION FOR SEQ ID NO: 157:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 157:

GAGTGACAAA TTGAGACCTG T                                         21

(2) INFORMATION FOR SEQ ID NO: 158:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 158:

CGTCAGCCTA AGGTGGACAT                                            20

(2) INFORMATION FOR SEQ ID NO: 159:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 159:

ACCGACAGAC TCTTGCCTC                                              19

(2) INFORMATION FOR SEQ ID NO: 160:

(i) SEQUENCE CHARACTERISTICS:
        (A) LENGTH: 20 base pairs (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 160:

TTGAGATGAC CCTGAGACTG                    20

(2) INFORMATION FOR SEQ ID NO: 161:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 161:

AGCAGAGCAA GACTGTCTCA                    20

(2) INFORMATION FOR SEQ ID NO: 162:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 162:

GACTCAAACA CCTTCATCCT A                  21

(2) INFORMATION FOR SEQ ID NO: 163:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 163:

GAGTGACAAA TTGAGACCTG T                  21

(2) INFORMATION FOR SEQ ID NO: 164:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 164:

CCTCAGCCTA AGGTGGACAT                    20

(2) INFORMATION FOR SEQ ID NO: 165:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 165:

GATGAAAGAA TGATAGATTA CAG                                    23

(2) INFORMATION FOR SEQ ID NO: 166:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 166:

ATCTTCTCAT GCCATATCTG C                                      21

(2) INFORMATION FOR SEQ ID NO: 167:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 167:

AGGAATTCAT GACTGAATAT AAACTTGT                               28

(2) INFORMATION FOR SEQ ID NO: 168:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 168:

ATCGAATTCT ATGCATATTA AAACAAGATT                             30

(2) INFORMATION FOR SEQ ID NO: 169:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 169:

GTAGGAATTC ACTTGTGCCC TGACTT                                 26

(2) INFORMATION FOR SEQ ID NO: 170:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 170:

```
CATCGAATTC CACTGACAAC CACCCTT                                               27

(2) INFORMATION FOR SEQ ID NO: 171:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 171:

GTAGGAATTC CAAGGCGCAC TGGCCTC                                               27

(2) INFORMATION FOR SEQ ID NO: 172:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 172:

ACTGAATTCT TCGTCTCCTC CACCGC                                                26

(2) INFORMATION FOR SEQ ID NO: 173:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 173:

TTGCCTACGC CAACAGCTCC                                                       20

(2) INFORMATION FOR SEQ ID NO: 174:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 174:

TTGCCTACGC CATCAGCTCC                                                       20

(2) INFORMATION FOR SEQ ID NO: 175:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 175:

TTGCCTACGC CACTAGCTCC                                                       20

(2) INFORMATION FOR SEQ ID NO: 176:
```

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: Genomic DNA (xi) SEQUENCE DESCRIPTION: SEQ ID NO: 176:

TTGCCTACGC CACAAGCTCC                                               20

(2) INFORMATION FOR SEQ ID NO: 177:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 177:

CACAAACATG CACCTCAA                                                 18

(2) INFORMATION FOR SEQ ID NO: 178:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 178:

TGCGCCGGCC TCTCCCA                                                  17

(2) INFORMATION FOR SEQ ID NO: 179:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 179:

TTGCCTACGC CACCAGCTCC                                               20

(2) INFORMATION FOR SEQ ID NO: 180:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 180:

CCGGTTCATG GCGCCCAT                                                 18

(2) INFORMATION FOR SEQ ID NO: 181:

(i) SEQUENCE CHARACTERISTICS:
        (A) LENGTH: 20 base pairs
        (B) TYPE: nucleic acid (C) STRANDEDNESS: single
        (D) TOPOLOGY: linear (ii) MOLECULE TYPE: Genomic DNA (xi) SEQUENCE DESCRIPTION: SEQ ID NO: 181:

GGAGCTGTTG GCGTAGGCAA                                                     20

(2) INFORMATION FOR SEQ ID NO: 182:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 182:

GGAGCTGATG GCGTAGGCAA                                                     20

(2) INFORMATION FOR SEQ ID NO: 183:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 183:

GGAGCTAGTG GCGTAGGCAA                                                     20

(2) INFORMATION FOR SEQ ID NO: 184:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 184:

GGAGCTTGTG GCGTAGGCAA                                                     20

(2) INFORMATION FOR SEQ ID NO: 185:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 185:

GGAGCTGGTG GCGTAGGCAA                                                     20

(2) INFORMATION FOR SEQ ID NO: 186:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 186:

ATGGGCGCCA TGAACCGG                                                        18

(2) INFORMATION FOR SEQ ID NO: 187:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO: 187:

TTGAGGTGCA TGTTTGTG                                                        18

(2) INFORMATION FOR SEQ ID NO: 188:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO: 188:

TGGGAGAGGC CGGCGCA                                                         17

(2) INFORMATION FOR SEQ ID NO: 189:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO: 189:

ACAAGTTTAT ATTCAGTCAT GAATTCCT                                             28

(2) INFORMATION FOR SEQ ID NO: 190:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO: 190:

AATCTTGTTT TAATATGCAT AGAATTCGAT                                           30

(2) INFORMATION FOR SEQ ID NO: 191:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO: 191:

AAGTCAGGGC ACAAGTGAAT TCCTAC                                               26

(2) INFORMATION FOR SEQ ID NO: 192:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 192:

AAGGGTGGTT GTCAGTGGAA TTCGATG        27

(2) INFORMATION FOR SEQ ID NO: 193:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 193:

GAGGCCAGTG CGCCTTGGAA TTCCTAC        27

(2) INFORMATION FOR SEQ ID NO: 194:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 194:

GCGGTGGAGG AGACGAAGAA TTCAGT        26

(2) INFORMATION FOR SEQ ID NO: 195:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 195:

GGACCTCGTG AATTACAATC        20

NUCLEIC ACID MUTATION DETECTION BY ANALYSIS OF SALIVA

CROSS REFERENCE TO RELATED APPLICATIONS

The present invention is a continuation of U.S. patent application Ser. No. 09/863,806, filed on May 22, 2001, now abandoned, which is a continuation of U.S. patent application Ser. No. 09/038,637, filed Mar. 10, 1998, now U.S. Pat. No. 6,235,470, which is a continuation-in-part of U.S. patent application Ser. No. 08/579,223, filed on Dec. 28, 1995, now U.S. Pat. No. 5,726,019, which is a continuation of U.S. patent application Ser. No. 08/152,313, filed Nov. 12, 1993, now U.S. Pat. No. 5,561,041. The disclosure of each of the prior applications is considered part of and is incorporated by reference in the disclosure of this application.

BACKGROUND OF THE INVENTION

1. Field of the Invention

The present invention relates generally to detection of a target nucleic acid sequence and specifically to early detection of preneoplasia or cancer in a subject by analysis of target mutant nucleic acid sequences in a saliva specimen from the subject.

2. Description of Related Art

An increasing body of evidence implicates somatic mutations as causally important in the induction of human cancers. These somatic mutations may accumulate in the genomes of previously normal cells, some of which may then demonstrate the phenotypes associated with malignant growth. Such oncogenic mutations may include a number of different types of alterations in DNA structure, including deletions, translocations and single nucleotide alterations. The latter, also known as point mutations, may frequently be involved in carcinogenesis, in that a variety of mutagenic chemicals induce such mutations. In addition, such mutations may occur spontaneously as a result of mistakes in DNA replication.

Advances in recombinant DNA technology have led to the discovery of normal cellular genes (proto-oncogenes and tumor suppressor genes) which control growth, development, and differentiation. Under certain circumstances, regulation of these genes is altered and cause normal cells to assume neoplastic growth characteristics. There are over 40 known proto-oncogenes and suppressor genes to date, which fall into various categories depending on their functional characteristics. These include, (1) growth factors and growth factor receptors, (2) messengers of intracellular signal transduction pathways, for example, between the cytoplasm and the nucleus, and (3) regulatory proteins influencing gene expression and DNA replication.

Point mutations have been directly implicated in the causation of many human tumors. Some tumors carry oncogenes of the ras gene family, which differ from their normal cellular counterpart proto-oncogenes by the presence of a point mutation at one of a limited number of sites in these genes. Similarly, point mutations in critical regions of tumor suppressor genes, such as p53, are often detected in tumor cells. These mutations represent qualitative changes in the tumor cell genome which distinguish these cells from normal cells and provide a basis for diagnosis of the genetic origin of a tumor under study. Identification of the mutations that have created active oncogenes may provide important diagnostic and prognostic clues for tumor development. For example, a number of mutations have been found to alter the 12th codon of the ras oncogenes, causing replacement of a normally present glycine by any of a number of alternative amino acid residues. Such amino acid substitutions create a potent transforming allele. Thus, the presence of a particular nucleotide substitution may be a strong determinant of the behavior of the tumor cell (e.g., its rate of growth, invasiveness, etc.). As a result, DNA probes for oncogene mutations have promise as diagnostic reagents in clinical oncology.

Among the various types of neoplasms, a number of those which are found in the lungs are associated with oncogenic mutations. Lung cancer is the leading cause of cancer related deaths in Western countries. The prognosis for patients with lung cancer is primarily dependent on the stage of the tumor at the time of clinical diagnosis. Currently, only 25 to 40 percent of all lung tumors are considered resectable at the time of initial assessment. Patients diagnosed early with stage 1 tumors have a 40-70% survival following surgical resection. An attempt at lung cancer screening through the use of tri-annual saliva cytology and annual chest x-ray has proven inadequate for the early detection of lung cancer. Alternatively, the finding that tumors progress through a series of well-defined genetic changes, including point mutations in oncogenes, has stimulated efforts to develop additional, non-invasive tests that could more reliably detect neoplasms of the lung. For example, U.S. Pat. No. 5,561,041 and U.S. Pat. No. 5,726,223 describe detection of neoplasia of the lung by analyzing sputum samples.

Other serious cancers are the head and neck cancers. Head and neck cancer remains a morbid and often fatal disease. Large tumor bulk and tumor extension are predictors of a local regional recurrence and poor outcome. Detection of occult neoplastic cells in surrounding surgical margins is a strong predictor of local regional recurrence resulting in a significant decrease in overall survival.

DNA contains unique sequences interspersed with moderately and highly repetitive DNA sequences. Variations in the repetitive sequence elements such as minisatellite (or variable number tandem repeat) DNA sequences and microsatellite (or variable simple sequence repeat) DNA sequences have been useful for chromosomal identification, primary gene mapping, and linkage analysis. Microsatellite DNA sequences are an especially common and highly polymorphic class of genomic elements in the human genome. One advantage to the use of repetitive sequence variations is the greater number of alleles present in populations compared with unique genetic sequence variations. Another advantage is the ability to readily detect sequence length variations using the polymerase chain reaction for the rapid and inexpensive analysis of many DNA samples.

Tumors progress through a series of genetic mutations. These genetic mutations can be used as specific markers for the detection of cancer. One set of genetic mutations that can be used to detect the presence of cancer is the loss of chromosomes. Diploid organisms, including humans, have pair of chromosomes for each member of the chromosomal set. Tumor cells will characteristically lose chromosomes, resulting in a single chromosome, rather than a pair of chromosomes, for each member of the chromosomal set. Chromosomal deletions and additions are an integral part of neoplastic progression and have been described in most kinds of cancers. A pair of chromosomes has two alleles for a genetic locus is heterozygous for that locus; therefore, the heterozygosity correlates to the cell having a pair of chromosomes. For years, these chromosomal deletions or amplifications were detected through the loss of heterozygosity.

Another of the genetic mutations used to detect the presence of cancer is genetic instability. Genetic recombination tends to occur most frequently at regions of the chromosome where the DNA is homologous (where the DNA has a high degree of sequence similarity). Where a DNA sequence is repetitive, the DNA homology is greater. The DNA homology occurs not only at the same genetic locus on the other pair of chromosomes, but also on other genetic loci or within the same locus on the same chromosome. Normal (non-tumor) cells tend to suppress this genetic recombination. Tumor cells, however, characteristically undergo increased genetic recombination. Where a DNA sequence is repetitive, genetic recombination can result in the loss of repeat DNA sequences or the gain of repeat DNA sequences at a genetic locus.

Microsatellite DNA instability has been described in human cancers. Microsatellite DNA instability is an important feature of tumors from hereditary non-polyposis colorectal carcinoma patients (Peltomaki et al., *Science*, 260: 810 (1993); Aaltonen et al., *Science*, 260: 812 (1993); Thibodeau et al., *Science*, 260: 816 (1993)). Microsatellite DNA instability by expansion or deletion of repeat elements has also been reported in colorectal, endometrial, breast, gastric, pancreatic, and bladder neoplastic tissues (Risinger et al., *Cancer Res.*, 53: 5100 (1993); Had et al., *Cancer Res.*, 53: 5087 (1993); Peltomaki et al., *Cancer Res.* 53: 5853 (1993); Gonzalez-Zulueta et al., *Cancer Res.* 53: 5620 (1993)).

Early detection of preneoplasia or cancer is crucial to increase the probability for treating such disorders. A non-invasive, simple screening test would provide health care workers with a tool for performing early diagnostic or prognostic screens.

SUMMARY OF THE INVENTION

The present invention arose from the unexpected finding that nucleic acid having a mutant nucleotide sequence associated with lung neoplasia or head and neck cancer is present in detectable levels in saliva specimens from patients having or at risk of having lung neoplasia or head and neck cancer.

As a consequence of this discovery, the present invention represents a significant advance over such techniques as tissue biopsy by providing a non-invasive, rapid, and accurate method for detecting mutant nucleotide sequences associated with lung neoplasia or neoplasia of the head and neck. The DNA amplification based approach of the invention can identify one cell carrying a mutant gene among a large excess (greater than 10,000) of normal cells. Based on this finding, it is now possible to detect various other target nucleic acids associated with other disease states. The present invention provides a method which can be used to screen high-risk populations to detect preneoplasia or cancer and to monitor high risk patients undergoing chemoprevention or chemotherapy.

In a first embodiment, the invention provides a method for detecting a neoplastic disorder of the head and neck or lung in a subject. The method includes providing a nucleic acid sample from a saliva specimen from the subject; and detecting the presence of a target mutant nucleotide sequence, wherein the presence of the target nucleotide sequence in the saliva is indicative of a neoplastic disorder of the head and neck or lung. Preferably, the subject is a human.

DETAILED DESCRIPTION OF THE INVENTION

Figure 1:
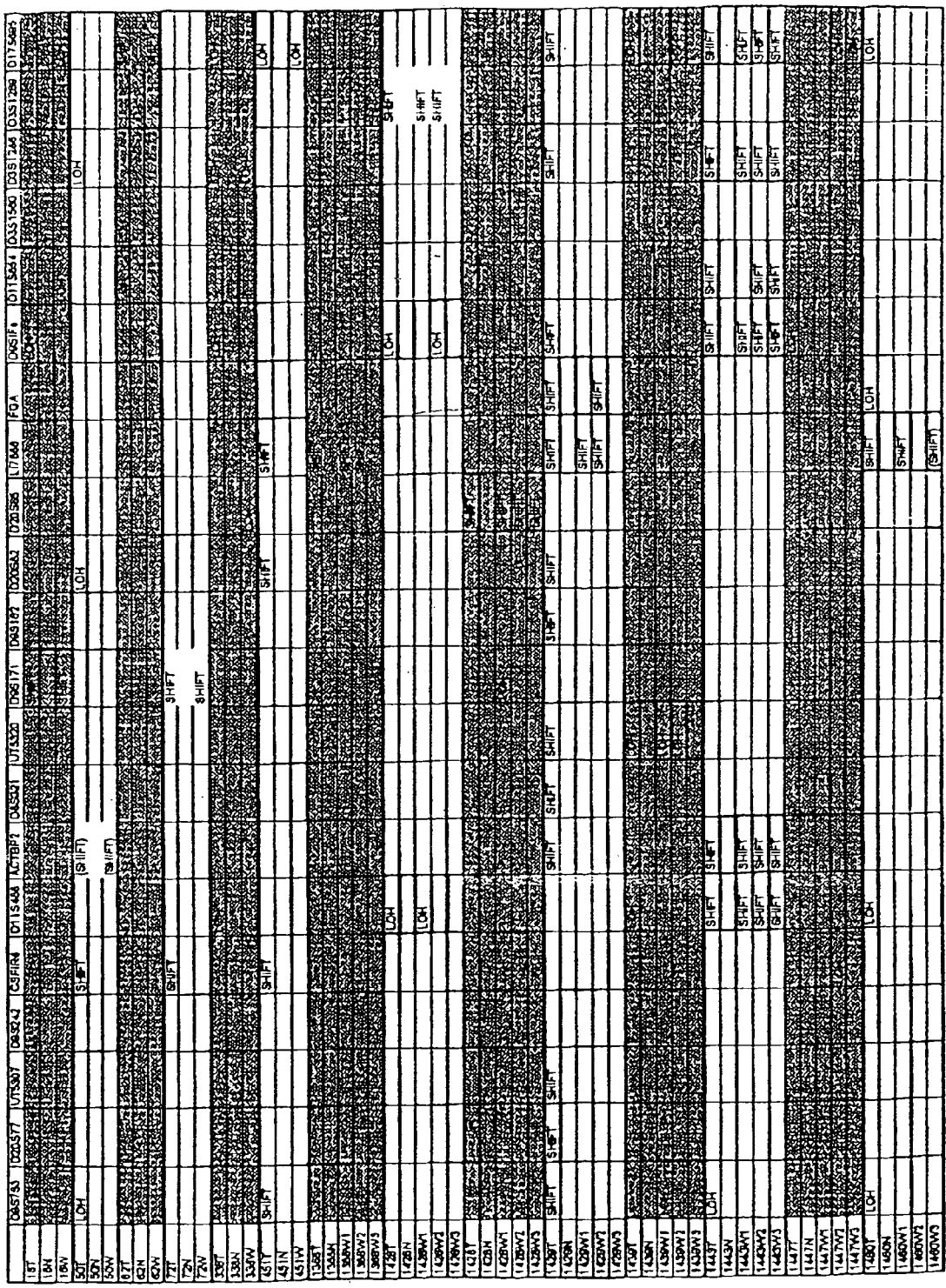
FIG. 1 shows a table of microsatellite analysis of many loci from saliva specimens.

The present invention relates to a method of detecting a preneoplasia or cancer in a subject by analyzing nucleic acid having a mutant nucleotide sequence present in saliva, wherein the presence of the mutant or altered nucleic acid sequence is associated with neoplasia or preneoplasia of the lung or head and neck.

In its broadest sense, the present invention allows the detection of any neoplastic disorder of any organ for any target nucleic acid sequence of diagnostic or therapeutic relevance, where the target nucleic acid sequence is present in saliva. Thus, the target nucleotide sequence may be, for example, a mutant nucleotide, a restriction fragment length polymorphism (RFLP), a nucleotide deletion, a nucleotide substitution, or any other mammalian nucleic acid sequence of interest.

Further, essentially any type of allelic imbalance can be detected in the saliva specimen. The term "allelic imbalance" refers to the chromosomal loss or gain that is characteristic of tumor cells. Diploid organisms, including humans, have a pair of chromosomes for each member of the chromosomal set. Tumor cells characteristically lose chromosomes, often resulting in a single chromosome, rather than a pair of chromosomes, for each member of a chromosomal set. Tumor cells also on occasion gain chromosomes, resulting in a two or more chromosomes, rather than a pair of chromosomes, for each member of the chromosomal set.

When a genetic locus on the chromosome has a different DNA sequence on each chromosome, a diploid organism has two alleles for that genetic locus. A pair of chromosomes with two alleles for a genetic locus is heterozygous. Whether a genetic locus is heterozygous for a subject can readily be determined by analyzing a sample of DNA from the normal (non-tumor) cells of the subject. Because microsatellite DNA is polymorphic, a genetic locus that contains microsatellite DNA will frequently be heterozygous. When a tumor cell loses or gains a chromosome, the result is that the cell loses or gains an additional copy of one of the alleles, causing an allelic imbalance or "loss of heterozygosity" (LOH). Methods of detection of LOH are described in co-pending U.S. patent application Ser. No. 08/968,733, which is herein incorporated by reference in its entirety.

Mutations in target nucleic acid can be identified in the method of the invention and used to screen for various cancer. "Mutation" is the process whereby changes occur in the quantity or structure of the genetic material of an organism. Mutations are permanent alterations in the genetic material which may lead to changes in phenotype. Mutation can involve modifications of the nucleotide sequence of a single gene, blocks of genes or whole chromosomes. Changes in single genes may be the consequence of point mutations, which involve the removal, addition or substitution of a single nucleotide base within a DNA sequence, or they can be the consequence of changes involving the insertion or deletion of large numbers of nucleotides. Modifications of whole chromosomes include both changes in number or structural changes involving chromosome abnormalities. Numerical chromosome mutations can involve multiples of the complete karyotype, termed "polyploidy", or they may involve deviations from the normal number of chromosomes, termed "aneuploidy". Mutations can arise spontaneously as a result of events such as errors in the fidelity of DNA replication or the movement of transposable genetic elements within genomes. They are also induced following exposure to chemical or physical mutagens. Such mutation-inducing agents include ionizing radiations, ultraviolet light and a diverse range of chemicals such as the alkylating agents, and polycyclic aromatic hydrocarbons, all of which are capable of interacting either directly or indirectly (generally following some metabolic biotransformations) with nucleic acids. The DNA lesions induced by such environmental agents may lead to modifications of the base sequence when the affected DNA is replicated or repaired and thus to a mutation.

An increasing body of evidence implicates somatic mutations as causally important in the induction of human cancers. These somatic mutations may accumulate in the genomes of previously normal cells, some of which may then demonstrate the phenotypes associated with malignant growth. Such oncogenic mutations may include a number of different types of alterations in DNA structure, including deletions, translocations and single nucleotide alterations. The latter, also known as point mutations, may frequently intervene in carcinogenesis, since a variety of mutagenic chemicals induce such mutations. In addition, such mutations may occur spontaneously as a result of mistakes in DNA replication. As used herein the term "mutant or mutated" as applied to a target neoplastic nucleotide sequence shall be understood to encompass a mutation, a restriction fragment length polymorphism, a nucleic acid deletion, or a nucleic acid substitution. A point mutation constitutes a single base change in a DNA strand, for example a G residue altered to a T. Such a mutation may alter the identity of the codon in which it lies thereby creating a missense mutation or nonsense mutation. Transition mutations involve the substitution of one purine in the DNA by another purine or one pyrimidine by another pyrimidine, that is A by G and vice versa, or T by C and vice versa. Transversions involve the replacement of a purine by a pyrimidine and vice versa. A missense mutation is a point mutation in which a codon is changed into one encoding amino acid other than that normally found at a particular position. A nonsense mutation is any mutation that converts a codon specifying an amino acid into one coding for termination of translation. A splicing mutation is any mutation affecting gene expression by affecting correct RNA splicing. Splicing mutations may be due to mutations at intron-exon boundaries which alter splice sites. A polyadenylation site mutant is a mutation of the consensus sequence required for addition of poly(A) to the 3' end of mature mRNA and which results in premature mRNA degradation. An insertion is any mutation caused by the insertion of a nucleotide or stretch of nucleotides into a gene. For example, naturally occurring insertion mutations can be the result of the transposition of transposable genetic elements.

Mutations that occur in somatic cells are not transmitted to the sexually produced offspring. However, such somatic mutations may be transferred to descendant daughter cells and mutations in some specific genes have been implicated in cancer. It is now clear that mutations may lead to the induction of cancer when they occur in one or more of a battery of normal genes referred to as the proto-oncogenes. Proto-oncogenes may be modified by a variety of mutational changes to produce the cancer-causing oncogenes of which more than forty have been identified. Proto-oncogenes play an essential part in the control of cell growth and differentiation and disruption of their normal activity by mutational events may lead to the aberrant growth characteristics observed in cancer cells.

The existence of proto-oncogenes which can be converted or activated to oncogenes by mutational events indicates a role for exposure to environmental agents (radiation and chemicals) in cancer induction. However, there are other types of genes, the tumor suppressor genes or anti-oncogenes, which contribute to cancer development only when they are inactivated or deleted. The normal forms of such genes appear to suppress the development of tumors whereas when only mutant forms are present tumors may develop. Such genes were identified because most tumors that lack functional copies of a suppressor gene (i.e., p53 or Rb) display two identically mutated (i.e., homozygous) alleles, while the unaffected tissues can be shown to carry one mutant tumor suppressor allele and one wild-type allele. Therefore, the loss of heterozygosity (LOH) at particular chromosome regions in tumor cells (compared with somatic cells from the same individual) is generally regarded as evidence for the unmasking of mutations in tumor suppressor genes located in these regions.

In addition, changes in DNA sequence which do not result in a detectable phenotypic change, termed "silent mutations", also occur in structural genes. Mutations in structural genes are silent if they do not change the amino acid inserted or if they result in substitution of a residue that does not affect protein function. Silent mutations can also be located outside protein-coding regions. A neutral mutation constitutes a genetic change which results in a phenotype which has no effect on an organism's fitness. Thus, even when the substitution results in the insertion of a different amino acid into a polypeptide, a missense mutation, the amino acid may be an acceptable substitute and may not lead to any significant change in the activity of the polypeptide. However, some missense amino-acid changes can have drastic effects upon the folding of polypeptide chains or upon the configuration of the active site of an enzyme. Other base substitutions may have drastic effects because they convert a triplet coding for an amino acid into one of the three termination signals which lead to the premature termination of polypeptide synthesis. Such nonsense changes are usually accompanied by the loss of function of the gene product.

When spontaneous or induced mutations are present in the germ cells of sexually reproducing organisms they may be transmitted to offspring. Such inherited mutations contribute to the background mutational load where they contribute to disease and disability. Inherited disease may be produced by both chromosome abnormalities and by mutations in single genes, although the influence of these two categories upon the observed mutation rate will be uneven.

In addition to variations in nucleotide sequence due to mutations, another major type of DNA polymorphism is a variation in the number tandemly repeated sequences at a particular location in the genome. The repeated sequence may be 10-60 nucleotides long, in which case the tandem array is termed a "minisatellite". Groups of shorter repeats (i.e., 2-5 nucleotides each) are termed "microsatellites". Microsatellites, also known as simple sequence repeats (SSRs) are highly variable polymorphic DNA sequences composed of a variable number of tandemly arranged simple di-, tri-, or tetranucleotide repeats. Generally, microsatellites are not localized in any particular chromosomal region but are randomly interspersed with other genomic DNA. Methods of detection of microsatellite markers in cancer are described in U.S. patent application Ser. No. 08/854,727, which is herein incorporated by reference in its entirety.

In one embodiment, the method of the invention is applicable for detection of mutant nucleotide sequences associated with benign as well as malignant neoplasias (cancer). In a preferred embodiment neoplasia of the lung or head and neck is detected, although the method can be used to detect any neoplastic mutant nucleotide sequence, regardless of origin, as long as the sequence is detectably present in saliva. For example, head and neck cancers shed cancer cells into saliva and can be detected. The term "head and neck cancer", as used herein, encompasses any carcinoma in tissues of the head and neck region of a subject. Such head and neck carcinomas would include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous call cancer, malignant melanoma, sinonasal undifferentiated carcinoma (SNUC) or blood neoplasia. Also included are carcinoma's of the regional lymph nodes including cervical lymph nodes, prelaryngeal lymph nodes, pulmonary juxtaesophageal lymph nodes and submandibular lymph nodes (Harrison's Principles of Internal Medicine (eds., Isselbacher, et al., McGraw-Hill, Inc., 13th Edition, pp1850-1853, 1994).

Numerous nucleic acids having mutant nucleotide sequences that produce an abnormal gene product are known to be associated with various neoplasias. Among the most common mutant nucleotide sequences are oncogenes and tumor suppressor genes, such as the K-ras mutant oncogene, p16, deleted in colon cancer (DCC), adenomatous polyposis coli(APC), familial adenomatous polyposis coli (FAP) and p53. Of special significance in the present invention is the detection of the K-ras mutant oncogene, p16, the p53 tumor suppressor gene (Vogelstein, Nature, 348:681, 1990), microsatellite loci, and LOH loci.

In order to analyze saliva specimens according to the method of the invention, it may be desirable to enrich for epithelial cells present in the specimen. This may be accomplished by mixing the sample with an epithelial cell specific monoclonal antibody, such as EBA-1 or Ber-Ep$_4$ (Can. Res. 53:3455, 1993) available from Dakopatts, Gestrop Denmark). Other epithelial cell specific antibodies will be known to those of skill in the art.

When it is desired to amplify the mutant nucleotide sequence before detection, this can be accomplished using oligonucleotide(s) which are primers for amplification. These unique oligonucleotide primers are based upon identification of the flanking regions contiguous with the mutant nucleotide sequence and are capable of substantially hybridizing with the flanking regions so that amplification can proceed. For example, in the case of K-ras, these oligonucleotide primers comprise sequences such as nucleotide sequence 5'-AGGAATTCATGACTGAATATAAACTTGT-3' (SEQ. ID NO. 167) and/or 5'-ATCGAATTCTATG-CATATTAAAACAAGATT-3' (SEQ. ID NO. 168) and sequences complementary thereto. In the case of p53, the oligonucleotide primers comprise sequences which are capable of hybridizing with the flanking nucleotide sequence, wherein the primers are 5'-GTAGGAATTCACTTGTGCCCTGACTT-3' (SEQ. ID NO. 169) and 5'-CATCGAATTCCACTGACAACCAC-CCTT-3' (SEQ. ID NO.170) (exons 5-6) and 5'-GTAG-GAATTCCAAGGCGCACTGGCCTC-3' (SEQ. ID NO. 171) and 5'-ACTGAATTCTTCGTCTCCTCCACCGC-3' (SEQ. ID NO. 172) for exons 7-8, and sequences complementary thereto.

The primers which can be used according to the method of the invention embrace oligonucleotides of sufficient length and appropriate sequence so as to provide specific initiation of polymerization of a significant number of nucleic acid molecules containing the target nucleic acid. In this manner, it is possible to selectively amplify the specific target nucleic acid sequence containing the nucleic acid of interest. Specifically, the term "primer" as used herein refers to a sequence comprising two or more deoxyribo-nucleotides or ribonucleotides, preferably at least eight, which sequence is capable of initiating synthesis of a primer extension product, which is substantially complementary to a target nucleic acid strand. The oligonucleotide primer typically contains 15-22 or more nucleotides, although it may contain fewer nucleotides.

Experimental conditions conducive to synthesis include the presence of nucleoside triphosphates and an agent for polymerization, such as DNA polymerase, and a suitable temperature and pH. The primer is preferably single stranded for maximum efficiency in amplification but may be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition.

Primers used according to the method of the invention are designed to be "substantially" complementary to each strand of target nucleotide sequence to be amplified. Substantially complementary means that the primers must be sufficiently complementary to hybridize with their respective strands under conditions which allow the agent for polymerization to function. In other words, the primers should have sufficient complementarily with the flanking sequences to hybridize therewith and permit amplification of the nucleotide sequence. Preferably, the 3' terminus of the primer that is extended has perfectly base paired complementarity with the complementary flanking strand.

Oligonucleotide primers used according to the invention are employed in any amplification process that produces increased quantities of target nucleic acid. Typically, one primer is complementary to the negative (−) strand of the mutant nucleotide sequence and the other is complementary to the positive (+) strand. Annealing the primers to denatured nucleic acid followed by extension with an enzyme, such as the large fragment of DNA Polymerase I (Klenow) or Taq DNA polymerase and nucleotides results in newly synthesized + and −strands containing the target nucleic acid. Because these newly synthesized nucleic acids are also templates, repeated cycles of denaturing, primer annealing, and extension results in exponential production of the region (i.e., the target mutant nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

The oligonucleotide primers for use in the invention may be prepared using any suitable method, such as conventional phosphotriester and phosphodiester methods or automated embodiments thereof. In one such automated embodiment, diethylphos-phoramidites are used as starting materials and may be synthesized as described by Beaucage, el al. (*Tetrahedron Letters*, 22:1859-1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

Any saliva specimen nucleic acid, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, including messenger RNA, wherein DNA or RNA may be single stranded or double stranded. If RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The mutant nucleotide sequence to be amplified, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

Where the target mutant nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means; the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (*CSH-Quantitative Biology*, 43:63, 1978) and techniques for using RecA are reviewed in C. Radding (*Ann. Rev. Genetics*, 16:405-437, 1982).

If the nucleic acid containing the target nucleic acid to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7-9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

In some amplification embodiments, the substrates, for example, the deoxyribonucleotide triphosphates dATP, dCTP, dGTP, and dTTP, are added to the synthesis mixture, either separately or together with the primers, in adequate amounts and the resulting solution is heated to about 90°-100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, E. coli DNA polymerase 1, Taq polymerase, Klenow fragment of E. coli DNA polymerase 1, T4 DNA polymerase, other available DNA polymerases, polymerase muteins, reverse transcriptase, ligase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each mutant nucleotide strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above. In any event, the method of the invention is not to be limited to the embodiments of amplification which are described herein.

The newly synthesized mutant nucleotide strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleosides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target mutant nucleotide sequence to the extent necessary for detection. The amount of the mutant nucleotide sequence produced will accumulate in an exponential fashion.

The amplified product may be detected by analyzing it by Southern blots without using radioactive probes. In such a process, for example, a small sample of DNA containing a very low level of mutant nucleotide sequence is amplified, and analyzed via a Southern blotting technique. The use of non-radioactive probes or labels is facilitated by the high level of the amplified signal.

Nucleic acids having a mutation detected in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008-1012, 1985), allele-specific oligonucleotide (ASO) probe analysis (Conner, et al., *Proc. Natl. Acad. Sci.* USA, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229-237, 1988). Thus, in a preferred embodiment where the mutant nucleotide sequence to be detected is K-ras, a hybridization probe is utilized which is capable of hybridizing with mutant nucleotide sequences comprising 5'-TTGCCTACGCCAACAGCTCC-3' ($Val^{12}$) (SEQ. ID NO. 173), 5'-TTGCCTACGCCATCAGCTCC-3' ($Asp^{12}$) (SEQ. ID NO. 174), 5'-TTGCCTACGCCACTAGCTCC-3' ($Ser^{12}$) (SEQ. ID NO. 175), or 5'-TTGCCTACGCCACAAGCTCC-3' ($Cys^{12}$) (SEQ. ID NO. 176) and sequences complementary thereto. Where the mutant nucleotide sequence to be detected is p53, a hybridization probe is utilized which is capable of hybridizing with mutant nucleotide sequences comprising 5'-CACAAACATGCACCTCAA-3' ($His^{273}$) (SEQ. ID NO. 177) or 5'-TGCGCCGGCCTCTCCCA-3' ($Gly^{281}$) (SEQ. ID NO. 178) and sequences complementary thereto. The wild type K-ras and wild type p53 are detected by hybridizing with nucleotide probes which hybridize with nucleotide sequences comprising 5'-TTGCCTACGCCACCAGCTCC-3' (SEQ. ID NO. 179) and 5'-CCGGTTCATGGCGCCCAT-3' (SEQ. ID NO. 180); respectively.

One method of in vitro amplification which can be used according to this invention is the polymerase chain reaction (PCR) described in U.S. Pat. Nos. 4,683,202 and 4,683,195. The term "polymerase chain reaction" refers to a method for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. The polymerase chain reaction is used to detect the existence of the defined sequence in the microsatellite DNA sample. Many polymerase chain methods are known to those of skill in the art and may be used in the method of the invention. For example, DNA can be subjected to 30 to 35 cycles of amplification in a thermocycler as follows: 95° C. for 30 sec, 52° to 60° C. for 1 min, and 72° C. for 1 min, with a final extension step of 72° C. for 5 min. For another example, DNA can be subjected to 35 polymerase chain reaction cycles in a thermocycler at a denaturing temperature of 95° C. for 30 sec, followed by varying annealing temperatures ranging from 54-58° C. for 1 min, an extension step at 70° C. for 1 min and a final extension step at 70° C.

Exemplary target nucleotide sequences of the invention, to which complementary oligonucleotide primers hybridize, include the following:

```
SEQ ID NO:1    5'-CTTGTGTCCCGGCGTCTG-3'

SEQ ID NO:2    5'-CAGCCCAGCAGGACCAGTA-3'
```

SEQ ID NO:3   5'-TGGTAACAGTGGAATACTGAC-3'
SEQ ID NO:4   5'-ACTGATGCAAAAATCCTCAAC-3'
SEQ ID NO:5   5'-GATGGGCAAACTGCAGGCCTGGGAAG-3'
SEQ ID NO:6   5'-GCTACAAGGACCCTTCGAGCCCCGTTC-3'
SEQ ID NO:7   5'-GATGGTGATGTGTTGAGACTGGTG-3'
SEQ ID NO:8   5'-GAGCATTTCCCCACCCACTGGAGG-3'
SEQ ID NO:9   5'-GTTCTGGATCACTTCGCGGA-3'
SEQ ID NO:10  5'-TGAGGATGGTTCTCCCCAAG-3'
SEQ ID NO:11  5'-AGTGGTGAATTAGGGGTGTT-3'
SEQ ID NO:12  5'-CTGCCATCTTGTGGAATCAT-3'
SEQ ID NO:13  5'-CTGTGAGTTCAAAACCTATGG-3'
SEQ ID NO:14  5'-GTGTCAGAGGATCTGAGAAG-3'
SEQ ID NO:15  5'-GCACGCTCTGGAACAGATTCTGGA-3'
SEQ ID NO:16  5'-ATGAGGAACAGCAACCTTCACAGC-3'
SEQ ID NO:17  5'-TCACTCTTGTCGCCCAGATT-3'
SEQ ID NO:18  5'-TATAGCGGTAGGGGAGATGT-3'
SEQ ID NO:19  5'-TGCAAGGAGAAAGAGAGACTGA-3'
SEQ ID NO:20  5'-AACAGGACCACAGGCTCCTA-3'
SEQ ID NO:21  5'-TCTCTTTCTTTCCTTGACAGGGTC-3'
SEQ ID NO:22  5'-CAGTGTGGTCCCAAATTTGAAATGG-3'
SEQ ID NO:23  5'-GTGCTGACTAGGGCAGCTT-3'
SEQ ID NO:24  5'-TGTGACCTGCACTCGGAAGC-3'
SEQ ID NO:25  5'-CCTTTCCTTCCTTCCTTCC-3'
SEQ ID NO:26  5'-CACAGTCAGGTCAGGCTATCAG-3'
SEQ ID NO:27  5'-TTTTTGAGATAGAGTCTCACTGTG-3'
SEQ ID NO:28  5'-CCACAGTCTAAGCCAGTCTGA-3'
SEQ ID NO:29  5'-GAATTTTGCTCTTGTTGCCCAG-3'
SEQ ID NO:30  5'-AGACTGAAGTCAATGAACAACAAC-3'
SEQ IP NO:31  5'-GGCTGTGAACATGGCCTAGGTC-3'
SEQ ID NO:32  5'-TTGGGGTGGTGCCAATGGATGTC-3'

Exemplary oligonucleotide primers, of the invention, include the following:

SEQ ID NO:33  5'-CAGACGCCGGGACACAAG-3'
SEQ ID NO:34  5'-TACTGGTCCTGCTGGGCTG-3'
SEQ ID NO:35  D21S1245(F) 5'-GTCAGTATTACCCTGTTACCA-3'
SEQ ID NO:36  D21S1245(R) 5'-GTTGAGGATTTTTGCATCAGT-3'
SEQ ID NO:37  5'-CTTCCCAGGCCTGCAGTTTGCCCATC-3'
SEQ ID NO:38  5'-GAACGGGGCTCGAAGGGTCCTTGTAGC-3'
SEQ ID NO:39  DRPLA(F) 5'-CACCAGTCTCAACACATCACCATC-3'
SEQ ID NO:40  DRPLA(R) 5'-CCTCCAGTGGGTGGGAAATGCTC-3'
SEQ ID NO:41  5'-TCCGCGAAGTGATCCAGAAC-3'
SEQ ID NO:42  5'-CTTGGGGAGAACCATCCTCA-3'
SEQ ID NO:43  D14S50(F) 5'-AACACCCCTAATTCACCACT-3'
SEQ ID NO:44  D14S50(R) 5'-ATGATTCCACAAGATGGCAG-3'
SEQ ID NO:45  FgA(F) 5'-CCATAGGTTTTGAACTCACAG-3'
SEQ ID NO:46  FgA(R) 5'-CTTCTCAGATCCTCTGACAC-3'
SEQ ID NO:47  D20548(F) 5'-TCCAGAATCTGTTCCAGAGCGTGC-3'
SEQ ID NO:48  D20548(R) 5'-GCTGTGAAGGTTGCTGTTCCTCAT-3'
SEQ ID NO:49  5'-AATCTGGGCGACAAGAGTGA-3'
SEQ ID NO:50  5'-ACATCTCCCCTACCGCTATA-3'
SEQ ID NO:51  5'-TCAGTCTCTCTTTCTCCTTGCA-3'
SEQ ID NO:52  5'-TAGGAGCCTGTGGTCCTGTT-3'
SEQ ID NO:53  D8S3G7(F) 5'-GACCCTGTCAAGGAAAGAAAGAGA-3'
SEQ ID NO:54  D8S3G7(R) 5'-CCATTTCAAATTTGGGACCACACTG-3'

-continued

```
SEQ ID NO:55    THO(F)      5'-AAGCTGCCCTAGTCAGCAC-3'
SEQ ID NO:56    THO(R)      5'-GCTTCCGAGTGCAGGTCACA-3'
SEQ ID NO:57    D11S488(F)  5'-mGGAAGGAAGGAAGGAAAGG-3'
SEQ ID NO:58    D11S488(R)  5'-CTGATAGCCTGACCTGACTGTG-3'
SEQ ID NO:59    D13S802(F)  5'-CACAGTGAGACTCTATCTCAAAAA-3'
SEQ ID NO:60    D13S802(R)  5'-TCAGACTGGCTTAGACTGTGG-3'
SEQ ID NO:61    D17S695(F)  5'-CTGGGCAACAAGAGCAAAATTC-3'
SEQ ID NO:62    D17S695(R)  5-mGTTGTTGTTCATTGACTTCAGTCT-3'
SEQ ID NO:63    D17S654(F)  5'-GACCTAGGCCATGTTCACAGCC-3'
SEQ ID NO:64    D17S654(R)  5'-GACATCCATTGGCACCACCCCAA-3'.
```

D13S1286 Dinucleotide Repeat

```
AFMc021xg5a (F)    GATCCACCAAAGCATATTATGA    (SEQ ID NO:65)
AFMc021xg5m (R)    TTAAGCATCTTGAATTTTGCCT    (SEQ ID NO:66)
```

(Dib. C Nature 380:152-4 1996)

D13S1289

```
AFMc031 zfla (F)   GTTTCTCCAGAACAGAACCAATAAG  (SEQ ID NO:67)
AFMc031 zflm (R)   TAACCATGTAAGCCAGTCCC       (SEQ ID NO:68)
```

Dib. C Nature 380:152-4 1996)

```
D13S1560
1E5F      GGCTGAGACATAAGACTCACTTGAAC       (SEQ ID NO:69)
1E5R      TCCATGATGGCTAATGATACTGAG         (SEQ ID NO:70)
D9S753
(F)       ACAGAGCAAGGTTGCCCAG              (SEQ ID NO:71)
(R)       TCCACTCAGCACCAACAGT              (SEQ ID NO:72)
FGA F     5'CCA TAG GTT TTG AAC TCA CAG    (SEQ ID NO:45)
FGA R     5'CTT CTC AGA TCC TCT GAC AC     (SEQ ID NO:46)
D4S243 F  5'TCA GTC TCT CTT TCT CCT TGC A  (SEQ ID NO:51)
D4S243 R  5'TAG GAG CCT GTG GTC CTG TT     (SEQ ID NO:52)
ACTBP2 F  5'AAT CTG GGC GAC AAG AGT GA     (SEQ ID NO:49)
ACTBP2 R  5'ACA TCT CCC CTA CCG CTA TA     (SEQ ID NO:50)
D8S307 F  5'GAC CCT GTC AAG GAA AGA AAG AGA (SEQ ID NO:53)
D8S307 R  5'CCA TTT CAA ATT TGG GAC CAC ACT G (SEQ ID NO:54)
D9S162 F  5'GCA ATG ACC AGT TAA GGT TC     (SEQ ID NO:73)
D9S162 R  5'AAT TCC CAC AAC AAA TCT CC     (SEQ ID NO:74)
IFN-A F   5'TGC GCG TTA AGT TAA TTG GTT    (SEQ ID NO:75)
```

-continued

```
IFN-A R      5'GTA AGG TGG AAA CCC CCA CT          (SEQ ID NO:76)

D9S171 F     5'AGC TAA GTG AAC CTC ATC TCT GTC T   (SEQ ID NO:77)

D9S171 R     5'ACC CTA GCA CTG ATG GTA TAG TCT     (SEQ ID NO:78)

D95747 F     5'GCC ATT ATT GAC TCT GGA AAA GAC     (SEQ ID NO:79)

D92747 R     5'CAG GCT CTC AAA ATA TGA ACA AAA T   (SEQ ID NO:80)

THO F        5'CAG CTG CCC TAG TCA GCA C           (SEQ ID NO:81)

THO R        5'GCT TCC GAG TGC AGG TCA CA          (SEQ ID NO:56)
             AGG CAA TAG AGA CCC TGT G             (SEQ ID NO:82)

D11S488 F    5' AAG GAA GGA AGG AAG GAA AGG        (SEQ ID NO:83)

D11S488 R    5' CTG ATA GCC TGA CCT GAC TGT G      (SEQ ID NO:58)
             GAT GAT GAA TTG TTA CTG AGA G         (SEQ ID NO:84)

D13S802 F    5' CAC AGT GAG ACT CTA TCT CAA AAA    (SEQ ID NO:59)

D13S802 R    5' TCA GAC TGG CTT AGA CTG TGG        (SEQ ID NO:60)

MJD F        5' CCA GTG ACT ACT TTG ATT CG         (SEQ ID NO:85)

MJD R        5' TGG CCT TTC ACA TGG ATG TGA A      (SEQ ID NO:86)

D16S310 F    5'GGG CAA CAA GGA GAG ACT CT          (SEQ ID NO:87)

D16S310 R    5'AAA AAA GGA CCT GCC TTT ATC C       (SEQ ID NO:88)

D16S476 F    5'TTG CAC TCC ACT CTG GGC A           (SEQ ID NO:89)

D16S476 R    5'TTG CCT TGG CTT TCT GTT GG          (SEQ ID NO:90)

D17S695 F    5'CTG GGC AAC AAG AGC AAA ATT C       (SEQ ID NO:61)

D17S695 R    5'TTT GTT GTT GTT CAT TGA CTT CAG TCT (SEQ ID NO:91)

D17S654 F    5'GAC CTA GGC CAT GTT CAC AGC C       (SEQ ID NO:63)

D17S654 R    5'GAC ATC CAT TGG CAC CAC CCC AA      (SEQ ID NO:64)

MBP F        5'GGA CCT CGT GAA TTA CAA TC          (SEQ ID NO:195)

MBP R        5'ATT TAC CTA CCT GTT CAT CC          (SEQ ID NO:92)

D18S51 F     5'GAG CCA TGT TCA TGC CCA CTG         (SEQ ID NO:93)

D18S51 R     5'CAA ACC CGA CTA ACC AGC AAC         (SEQ ID NO:94)

D20S82       GCC TTG ATC ACA CCA CTA CA            (SEQ ID NO:95)

D20S82       GTG GTC ACT AAA GTT TCT GCT           (SEQ ID NO:96)

D20S85       ATT ACA GTG TGA GAC CCT G             (SEQ ID NO:97)

D20S85       GAG TAT CCA GAG AGC TAT TA            (SEQ ID NO:98)

D20S94       TTG CTC CAA CCA GGA GGC A             (SEQ ID NO:99)

D20S94       GAA CCA AGG AAG TTG TTC AAC           (SEQ ID NO:100)

D20S77       GCA GTG AGT TCA TAT GGC TA            (SEQ ID NO:101)
             GTT TCT CTG TTC AGC ACT TC            (SEQ ID NO:102)

PPT          TGG CGA GAC TCC ATC AAA G             (SEQ ID NO:103)
             CCT TTT AAG CTG CAA CAA TTT C         (SEQ ID NO:104)

CSF1R.4      CAG GTT GCT AAC CAC CCT GT            (SEQ ID NO:105)
             GTG CAC ACT TGG ACA GCA TT            (SEQ ID NO:106)

D14S125      CTG ACT CCA GAG CCT GGG               (SEQ ID NO:107)
             GGT TGA ATG TGG CGT GTT C             (SEQ ID NO:108)

D14S50       AAC ACC CCT AAT TCA CCA CT            (SEQ ID NO:43)
             ATG ATT CCA CAA GAT GGC AG            (SEQ ID NO:44)
```

-continued

| | | |
|---|---|---|
| FGA | CCA TAG GTT TTG AAC TCA CAG | (SEQ ID NO:45) |
| | CTT CTC AGA TCC TCT GAC AC | (SEQ ID NO:46) |
| D9S252 | ACA ATG AAC ATC CAT ATA CCC | (SEQ ID NO:109) |
| | ACC ATG ATT TGT CAA CTC CTA | (SEQ ID NO:110) |
| D14S140 | GCA TCT TGT TAG GGC AGC C | (SEQ ID NO:111) |
| | CCT GCA GAT TTT TGA TTT ACC | (SEQ ID NO:112) |
| TBP | GAC CCC ACA GCC TAT TCA GA | (SEQ ID NO:113) |
| | TTG ACT GCT GAA CGG CTG CA | (SEQ ID NO:114) |
| APOB | GAA GAT TGC AGA GCT TTC TGC CAC | (SEQ ID NO:115) |
| | GTA AGT TCT CCT GGA GCA AGC TTC | (SEQ ID NO:116) |
| ACPP | GAG GCT ACA GTA AGC CAA GAG TGC | (SEQ ID NO:117) |
| | GCC TTC AAA AAT GCA AGG ATT ACA | (SEQ ID NO:118) |
| D8S306 | GTT GAA CAG GAG CAG TGA GAG | (SEQ ID NO:119) |
| | AGA GAA AGA GAG ACA GAA AGA GAG A | (SEQ ID NO:120) |
| L17686 | GCA CCA ATG CTC CAG AAA TG | (SEQ ID NO:121) |
| | TCA TGG TGC CAT GAT AGG AG | (SEQ ID NO:122) |
| D8S341 | TAG GTA GTA AAC TTC ATA CAC G | (SEQ ID NO:123) |
| | CTC ATC TGC CTA TAT CAC AGC | (SEQ ID NO:124) |
| Z35281 | TGA TCT TCA AAG AGA GTT CCG | (SEQ ID NO:125) |
| | AGT TCG ATA GCA CTC GCC GT | (SEQ ID NO:126) |
| G08270 | TGG CGC TGA TGC TCC ACA TTC | (SEQ ID NO:127) |
| | CTG GCT GAC AGA TAA AGC ACT | (SEQ ID NO:128) |
| G29028 | GCA GTG AGC TGA GAT AAT GC | (SEQ ID NO:129) |
| | TCA CTA GCA GAT GCG ATA ATG | (SEQ ID NO:130) |
| UT5307 | GGA TAT AGC TGG CAA TGG C | (SEQ ID NO:131) |
| | TCG GAA TGC CTA CTT CCC AG | (SEQ ID NO:132) |
| D9S242 | GTG AGA GTT CCT TCT GGC | (SEQ ID NO:133) |
| | ACT CCA GTA CAA GAC TCT G | (SEQ ID NO:134) |
| D9S758 | AGC CTG GGT GAC AAA GCA AG | (SEQ ID NO:135) |
| | GCT CCA CAC CAC ACA CAT G | (SEQ ID NO:136) |
| D9S778 | AGA TCG CGC CAT TGT ACT C | (SEQ ID NO:137) |
| | AGC TCA GGG CAT TCT GTG AA | (SEQ ID NO:138) |
| D9S769 | GGA CTG CAT CTT AGG TGC TA | (SEQ ID NO:139) |
| | CAC CAA TGC AGT CTA GCC T | (SEQ ID NO:140) |
| D9S737 | ACG CTG GGC TAA TTC TTG | (SEQ ID NO:141) |
| | AGA GGC CAG GAG TTT GAG | (SEQ ID NO:142) |
| L17835 | TTG CAC CAC TAT ACT CCA GC | (SEQ ID NO:143) |
| | TCA GTT TAA GGT TCT CAC CTG | (SEQ ID NO:144) |
| D17S846 | TCC TTT GTT GCA GAT TTC TTC | (SEQ ID NO:145) |
| | TGC ATA CCT GTA CTA CTT CAG | (SEQ ID NO:146) |
| D11S488 | AGG CAA TAG AGA CCC TGT G | (SEQ ID NO:147) |
| | GAT GAT GAA TTG TTA CTG AGA G | (SEQ ID NO:148) |
| D9S243 | AAG GGG TGT CAT GTA GCA AG | (SEQ ID NO:149) |
| | CAA TCC AGG GAA GTT TCC AT | (SEQ ID NO:150) |
| D9S242 | GTG AGA GTT CCT TCT GGC | (SEQ ID NO:151) |
| | ACT CCA GTA CAA GAC TCT G | (SEQ ID NO:152) |
| D9S759 | TGG CAG TGG AAG ACT CTT T | (SEQ ID NO:153) |
| | TGA GGA TTC CAG CAA TGC T | (SEQ ID NO:154) |
| X80250 | TCA CCA CTG CAC TCC AGC CT | (SEQ ID NO:155) |
| | GGA CTC ACC TTA TGC CAT GT | (SEQ ID NO:156) |
| X912531 | GAG TGA CAA ATT GAG ACC TGT | (SEQ ID NO:157) |
| | CGT CAG CCT AAG GTG GAC AT | (SEQ ID NO:158) |
| UT5320 | ACC GAC AGA CTC TTG CCT C | (SEQ ID NO:159) |
| | TTG AGA TGA CCC TGA GAC TG | (SEQ ID NO:160) |

-continued

```
D11S554    AGC AGA GCA AGA CTG TCT CA        (SEQ ID NO:161)
           GAC TCA AAC ACC TTC ATC CTA       (SEQ ID NO:162)

X91253     GAG TGA CAA ATT GAG ACC TGT       (SEQ ID NO:163)
           CCT CAG CCT AAG GTG GAC AT        (SEQ ID NO:164)

D8S321     GAT GAA AGA ATG ATA GAT TAC AG    (SEQ ID NO:165)
           ATC TTC TCA TGC CAT ATC TGC       (SEQ ID NO:166)
```

Those of ordinary skill in the art will know of various amplification methodologies which can also be utilized to increase the copy number of target nucleic acid. Microsatellite DNA sequence detected in the method of the invention can be further evaluated, detected, cloned, sequenced, and the like, either in solution or after binding to a solid support, by any method usually applied to the detection of a specific DNA sequence such as another polymerase chain reaction, oligomer restriction (Saiki el al., *Bio/Technology* 3: 1008-1012 (1985)), allele-specific oligonucleotide (ASO) probe analysis (Conner et al., *Proc. Natl. Acad Sci. USA* 80: 278 (1983), oligonucleotide ligation assays (OLAs) (Landegren et al., *Science* 241: 1077 (1988)), and the like. Molecular techniques for DNA analysis have been reviewed (Landegren et al., *Science*, 242: 229-237 (1988)). Following DNA amplification, the reaction product may be detected by Southern blot analysis, without using radioactive probes. In such a process, for example, a small sample of DNA containing a very low level of microsatellite DNA nucleotide sequence is amplified, and analyzed via a Southern blotting technique. The use of non-radioactive probes or labels is facilitated by the high level of the amplified signal. In a preferred embodiment of the invention, one nucleoside triphosphate is radioactively labeled, thereby allowing direct visualization of the amplification product by autoradiography. In another embodiment, amplification primers are fluorescent labeled and run through an electrophoresis system. Visualization of amplified products is by laser detection followed by computer assisted graphic display.

In an embodiment of the invention, purified nucleic acid fragments containing intervening sequences or oligonucleotide sequences of 10-50 base pairs are radioactively labelled. The labelled preparations are used to probe nucleic acid from saliva by the Southern hybridization technique. Nucleotide fragments from saliva, before or after amplification, are separated into fragments of different molecular masses by gel electrophoresis and transferred to filters which bind nucleic acid. After exposure to the labelled probe, which will hybridize to nucleotide fragments containing target nucleic acid sequences, binding of the radioactive probe to target nucleic acid fragments is identified by autoradiography (see *Genetic Engineering*, 1, ed. Robert Williamson, Academic Press, (1981), 72-81). Alternatively, nucleic acid from saliva can be bound directly to filters to which the radioactive probe selectively binds nucleic acids having the sequence of interest specific sequences and the degree of binding is quantitated by directly counting the radioactive emissions.

Where the target nucleic acid is not amplified, detection using an appropriate hybridization probe may be performed directly on the separated mammalian nucleic acid. In those instances where the target nucleic acid is amplified, detection with the appropriate hybridization probe would be performed after amplification.

The probes of the present invention can be used for examining the distribution of the specific fragments detected, as well as the quantitative (relative) degree of binding of the probe for determining the occurrence of specific strongly binding (hybridizing) sequences, thus indicating the likelihood for an individual to be at low risk or high risk for neoplastic disease, such as a lung carcinoma. Further cloning allows specific evaluation of the number of mutant nucleotides (i.e., mutant cells) allowing a precise estimate of risk to develop neoplastic disease.

For the most part, the probe will be labelled with an atom or inorganic radical, most commonly using radionuclides, but also perhaps heavy metals. Conveniently, a radioactive label may be employed. Radioactive labels include $^{32}$P, $^{125}$I, $^{3}$H, $^{14}$C, or the like. Any radioactive label may be employed which provides for an adequate signal and has sufficient half-life. Other labels include ligands, which can serve as a specific binding pair member for a labelled ligand, and the like. A wide variety of labels have been employed in immunoassays which can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization. Other considerations will be ease of synthesis of the probe, readily available instrumentation, ability to automate, convenience, and the like.

The manner in which the label is bound to the probe will vary depending upon the nature of the label. For a radioactive label, a wide variety of techniques can be employed. Commonly employed is nick translation with an a $^{32}$P-dNTP or terminal labeling with radioactive $^{32}$P employing $\gamma^{32}$P-ATP and T4 polynucleotide kinase. Alternatively, nucleotides can be synthesized where one or more of the elements present are replaced with a radioactive isotope, e.g., hydrogen with tritium. If desired, complementary labelled strands can be used as probes to enhance the concentration of hybridized label.

Where other radionuclide labels are involved, various linking groups can be employed. A terminal hydroxyl can be esterified, with inorganic acids, (e.g., $^{32}$P phosphate), or $^{14}$C organic acids, or else esterified to provide linking groups to the label. Alternatively, intermediate bases may be substituted with activatable linking groups which can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2,3-dihydrophthalazinediones (e.g., luminol).

The probe can be employed for hybridizing to a nucleotide sequence affixed to a water insoluble porous support. Depending upon the source of the nucleic acid, the manner in which the nucleic acid is affixed to the support may vary.

Those of ordinary skill in the art know, or can easily ascertain, different supports which can be used in the method of the invention.

Any mammalian cells present in saliva are treated to liberate their nucleic acid. The target sequences containing mutant nucleotides are amplified by PCR or other aforementioned techniques. The amplified nucleic acid from a saliva specimen is spotted or spread onto a filter to provide a plurality of individual portions. The filter is an inert porous solid support (e.g., nitrocellulose). The lysing and denaturation of nucleic acid, as well as the subsequent washings, can be achieved with an appropriate solution for a sufficient time to lyse the cells and denature the nucleic acid. For lysing, chemical lysing will conveniently be employed, as described previously for the saliva lysis buffer. Other denaturation agents include elevated temperatures, organic reagents (e.g., alcohols, amides, amines, ureas, phenols and sulfoxides) or certain inorganic ions (e.g., thiocyanate and perchlorate).

In a preferred embodiment, the amplified nucleic acid containing the mutant nucleotide is be cloned into a vector (e.g., plasmid, cosmid, bacteriophage) utilizing the 5' restriction sites contained within the amplification primers. Each clone contains one copy of the amplified target sequence. The clone is transferred to filters as described above, followed by denaturation. Hybridization with an oligonucleotide specific for the mutant nucleotide allows the detection of one mutant nucleotide among 10,000 normal nucleotides which differ at a single base pair.

After denaturation, the filter is washed in an aqueous buffered solution, such as Tris, generally at a pH of about 6 to 8, usually 7. One or more washings may be involved, conveniently using the same procedure as employed for the lysing and denaturation. After the lysing, denaturing, and washes have been accomplished, the nucleic acid spotted filter is dried at an elevated temperature, generally from about 50° C. to 70° C. Under this procedure, the nucleic acid is fixed in position and can be assayed with the probe when convenient.

Pre-hybridization may be accomplished by incubating the filter at a mildly elevated temperature for a sufficient time with the hybridization solution without the probe to thoroughly wet the filter. Various hybridization solutions may be employed, comprising from about 20% to 60% volume, preferably 30%, of an inert polar organic solvent. A common hybridization solution employs about 50% formamide, about 0.5 to 1M sodium chloride, about 0.05 to 0.1M sodium citrate, about 0.05 to 0.2% sodium dodecylsulfate, and minor amounts of EDTA, ficoll (about 300-500 kD), polyvinylpyrrolidone, (about 250-500 kD) and serum albumin. Also included in the hybridization solution will generally be from about 0.5 to 5 mg/ml of sonicated denatured DNA (e.g., calf thymus or salmon sperm) and optionally from about 0.5 to 2% wt/vol glycine. Other additives may also be included, such as dextran sulfate of from about 100 to 1,000 kD and in an amount of from about 8 to 15 weight percent of the hybridization solution.

The particular hybridization technique is not essential to the invention. Other hybridization techniques are described by Gall and Pardue, *Proc. Natl. Acad. Sci.* 63:378, 1969; and John, et al., *Nature*, 223:582, 1969. As improvements are made in hybridization techniques they can readily be applied in the method of the invention.

The amount of labelled probe which is present in the hybridization solution will vary widely, depending upon the nature of the label, the amount of the labelled probe which can reasonably bind to the filter, and the stringency of the hybridization. Generally, substantial excess over stoichiometric concentrations of the probe will be employed to enhance the rate of binding of the probe to the fixed target nucleic acid.

Various degrees of stringency of hybridization may be employed. The more severe the conditions, the greater the complementarily that is required for hybridization between the probe and the single stranded target nucleic acid sequence for duplex formation. Severity can be controlled by temperature, probe concentration, probe length, ionic strength, time, and the like. Conveniently, the stringency of hybridization is varied by changing the polarity of the reactant solution by manipulating the concentration of formamide in the range of 20% to 50%. Temperatures employed will normally be in the range of about 20° C. to 80° C., usually 30° C. to 75° C. (see, generally, *Current Protocols in Molecular Biology*, Ausubel, ed., Wiley & Sons, 1989).

After the filter has been contacted with a hybridization solution at a moderate temperature for a period of time sufficient to allow hybridization to occur, the filter is then introduced into a second solution having analogous concentrations of sodium chloride, sodium citrate and sodium dodecylsulfate as provided in the hybridization solution. The time for which the filter is maintained in the second solution may vary from five minutes to three hours or more. The second solution determines the stringency, dissolving cross duplexes and short complementary sequences. After rinsing the filter at room temperature with dilute sodium citrate-sodium chloride solution, the filter may now be assayed for the presence of duplexes in accordance with the nature of the label. Where the label is radioactive, the filter is dried and exposed to X-ray film.

The label may also be labeled with a fluorescence moiety which can then be probed with a specific antifluorescence antibody. Conjugated to this antibody is horseradish peroxidase enzyme, for example, able to catalyze a chemiluminescent reaction. Production of light can then be seen on rapid exposure to film.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method.

In general, one of the container means may comprise a hybridization probe which is or can be detectably labelled. A second container may comprise a saliva/epithelial cell lysis buffer. The kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radionuclide label.

The method of the invention provides the basis for a kit useful for the detection of a target mutant nucleic acid sequence in a saliva specimen. The presence of a target mutant nucleic acid sequence in the saliva is indicative of the presence of a neoplastic disorder (e.g., of the head and neck or lung). The kit includes a carrier means being compartmentalized to receive therein one or more containers. For example, a first container contains a nucleic acid hybridization probe which hybridizes to the target nucleic acid. For example, the target nucleic acid to which the probe hybridizes is selected from the group consisting of 5'-TTGCCTACGCCAACAGCTCC-3',    (SEQ. ID NO. 173)
5'-TTGCCTACGCCATCAGCTCC-3',    (SEQ. ID NO. 174)
5'-TTGCCTACGCCACTAGCTCC-3',    (SEQ. ID NO. 175)
5'-TTGCCTACGCCACAAGCTCC-3',    (SEQ. ID NO. 176)
5'-CACAAACATGCACCTCAA-3',      (SEQ. ID NO. 177)
5'-TGCGCCGGCCTCTCCCA-3',       (SEQ. ID NO. 178)
5'-TTGCCCACGCCACCAGCTCC-3',    (SEQ. ID NO. 179) and
5'-CCGGTTCATGGCGCCCAT-3'.      (SEQ. ID NO. 180)

Other target nucleic acid sequences can be determined by those of skill in the art and include, but are not limited to sequences of tumor suppressor genes (e.g., p53, p16) oncogenes (e.g., K-ras), microsatellite markers, and the like. In addition, the kit may include a second container containing a means for detecting hybridization of the probe with the target nucleic acid. Such reporter means include a biotin-binding protein, such as avidin or streptavidin, bound to a reporter molecule. such as an enzymatic, florescent, or radionuclide label. Other reporter means and labels are well known in the art. The kit may also include an amplification polymerase and deoxyribonucleotide(s). The kit may further include nucleic acid amplification buffer. Preferably, the reagent that modifies unmethylated cytosine is bisulfite. The kit of the invention is intended to provide the reagents necessary to perform nucleic acid hybridization analysis as described herein.

Techniques for obtaining saliva are usually based on collection by aspiration or absorption to material that is chewed or placed somewhere in the mouth, or any method which results in oral evacuation. Saliva acquisition can be accomplished by any means which allows for the isolation of a sample from a subject that results in a sufficient quantity of fluid being obtained for testing. Such methods can include, for example, the use of a sterile, absorbent cotton swab (e.g., with a serrated edge designed for use in collecting body fluids or cells. The swab head can be designed to fit into a micro-centrifuge tube or combined with a mini-vial transport system. The device can further consist of a plastic cylinder fitted at one end with a plug-gasket-filter assembly. The filter typically has an appropriate pore size to allow passage of a clean test fluid into a container while particulates are eliminated. Preferably, the saliva sample is collected in saline (e.g., about 0.9% NaCl solution).

Oral rinses and other methods of obtaining saliva can be utilized in the methods of the invention. Various personnel, including dental personnel and other medical or non-medical workers may collect the saliva sample for further analysis as described herein. Examples of saliva collection are described in Example 1 herein.

OMNI-SAL®is a painless, non-invasive saliva collection system designed to maintain sample integrity. An alternative to blood or urine, saliva may be collected at any location with minimal training. The system consists of a sterile collection device with patented volume adequacy indicator, and a transport tube containing a stabilizing buffer.

The above disclosure generally describes the present invention. A more complete understanding can be obtained by reference to the following specific examples which are provided herein for purposes of illustration only and are not intended to limit the scope of the invention.

EXAMPLE 1

Saliva Collection Protocol

Saliva can be obtained from a subject by a number of ways that will be apparent to those of skill in the art, including oral rinses, swabs, suction, and the like. The following are intended to be non-limiting examples of saliva extraction from a subject.

1. Pre-operative oral rinse—The patient or control subject gargles and rinses with 25 cc of sterile 0.9% NaCl for 15 seconds. If sample must be collected intraoperatively, the saline is placed in the oral cavity of the supine anesthetized patient and collected using a suction trap.

2. Intraoperative tumor swab—The surgeon uses a sterile cotton-tipped applicator or powder-free gloved finger to swab the surface of the epithelial lesion. The exfoliated cells are collected in 25 cc of sterile 0.9% NaCl. If the patient will not be treated surgically, this specimen is collected in clinic.

3. Intraoperative nonspecific oral cavity swab—The surgeon uses a cotton-tipped applicator or powder-free gloved finger to swab the oral cavity and oropharynx, including as much of the hypopharynx as feasible. The exfoliated cells are collected in 25 cc of sterile 0.9% NaCl. If the patient will not be treated surgically, this specimen is collected in clinic.

4. The investigator places the rinse specimens in 50 ml Sarstedt conical centrifuge tubes and spins at 2500 rpm for 15 minutes. The supernatant is decanted off and the pellet is used for DNA extraction.

EXAMPLE 2

DNA was isolated from the saliva samples by standard methods such as those described in U.S. Pat. No. 5,561,041 and U.S. Pat. No. 5,726,23, which methods are herein incorporated by reference.

Microsatellite analysis was performed by using standard PCR techniques known in the art. An exemplary experiment is as follows:

1. End labeling of the primer

| –1.5 ml tube (small) | 10 µl | ddH20 |
| --- | --- | --- |
| | 5 µl | primer (F or R) |
| | 2 µl | Buffer (T4 buffer) |
| | 1 µl | T4-Kinase |
| | 2 µl | $P^{32}$ γATP |
| Total volume | 20 µl | |

Incubation for 30 min. In 37° C.

2. In PCR room setup tubes/wells for PCR analysis (template DNA)

Dilute genomic DNA to a working concentration of 10 ng/µl; normal and tumor DNA for each sample to be analysed (Label) N and T for each sample and place 2.5 µl into corresponding tubes/wells 3. Prepare reaction mix for each PCR reaction corresponding the number of reaction/wells Primers F and R diluted to 100 ng/µl working stock/dilution 4. Take 7.5 µl of the reaction mix and add to the template tube prepared in step 2, to total reaction volume of 10 µl 5. Add 1 drop of mineral oil on top of each tube 6. Place tubes/wells in PCR block and perform PCR reaction:

| optimized temp. | 95° C. for 1 min | |
|---|---|---|
| | 50-58° C. for 1 min | |
| | 72° C. for 1 min | 35 Cycles |
| | 72° C. for 1 min | 1 Cycle |

7. Complete PCR reaction and dilute with 4 μl Stop-buffer

8. Load 3 μl of reaction mix onto 7M Formamide Denaturing Gel and electrophorese for 2-5 hours corresponding to the size of the product 9. Transfer gel to 3 mm Whatman paper and place in cassette.

10. Place film onto a gel and develop after 8-10 hours at −80° C.

Results (N=32)

1. Study #1: Cases with tumor-specific microsatellite alterations detected in all exfoliated epithelial cell samples using a panel of 8 microsatellite markers: 14/18(77%).
   a. Cases detected by shift markers: 10/18(55%).
   b. Cases detected by LOH markers: 7/18(38%).
   c. Cases detected by both shift and LOH markers: 3/14(21%).

2. Study #2: Cases with tumor-specific microsatellite alterations detected in all
   OMNI-SAL® is a painless, non-invasive saliva collection system designed to maintain sample integrity. An alternative to blood or urine, saliva may be collected at any location with minimal training. The system consists of a sterile collection device with patented volume adequacy indicator, and a transport tube containing a stabilizing buffer. exfoliated epithelial cell samples using a panel of 21 microsatellite markers: 12/14(86%).
   a. Cases detected by shift markers: 9/14 (64%)
   b. Cases detected by LOH markers: 4/14 (29%).
   c. Cases detected by both shift and LOH markers: 2/14 (14%).

3. Detection rate combining the two pilot studies (n=32): 26/32(81%).

Summary of Microsatellite Analysis

Microsatellite DNA markers have been commonly used to accurately detect genetic alterations in primary tumors. Saliva from 22 patients with known neoplastic lesions of the oral, pharyngeal and laryngeal mucosa were analyzed molecularly by microsatellite analysis using methods described herein. Using 8 informative tetra-nucleotide microsatellite markers, 15 of 22 (68%) patients displayed microsatellite changes in saliva matching those seen in the respective tumor. 4 of 15 (27%) patients with genetic alterations in their saliva displayed loss of heterozygosity (LOH) in saliva and tumor DNA, 8 patients displayed microsatellite instability in saliva and tumor DNA and 3 patients displayed both LOH and microsatellite instability. Saliva DNA of 15 normal controls was analyzed by this molecular method and none were found to harbor microsatellite instability. This data suggests that PCR based microsatellite analysis using a panel of selected oligonucleotide markers susceptible to shift alterations, is a very sensitive method of detection and surveillance of neoplastic lesions of the head and neck, e.g., oropharynx.

Figure 2:
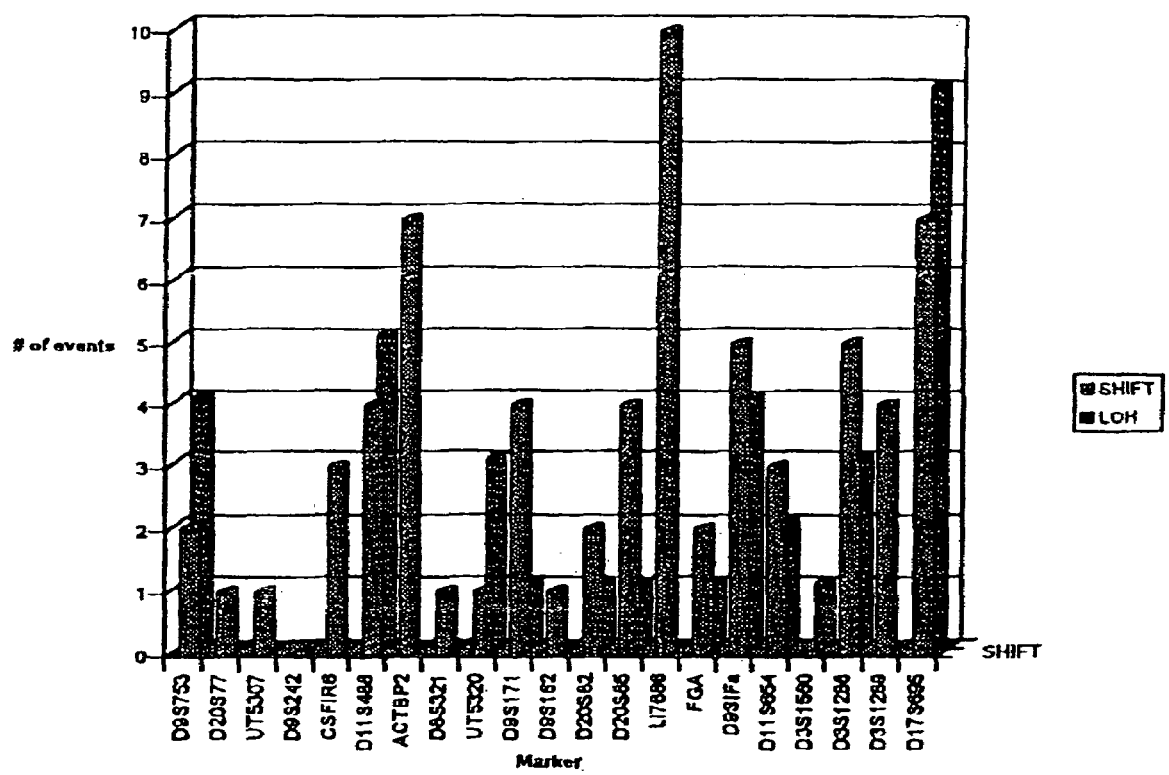
FIG. 2 shows a graph of tumor detection in saliva by shift markers versus loss of heterozygosity (LOH).
Figure 3:
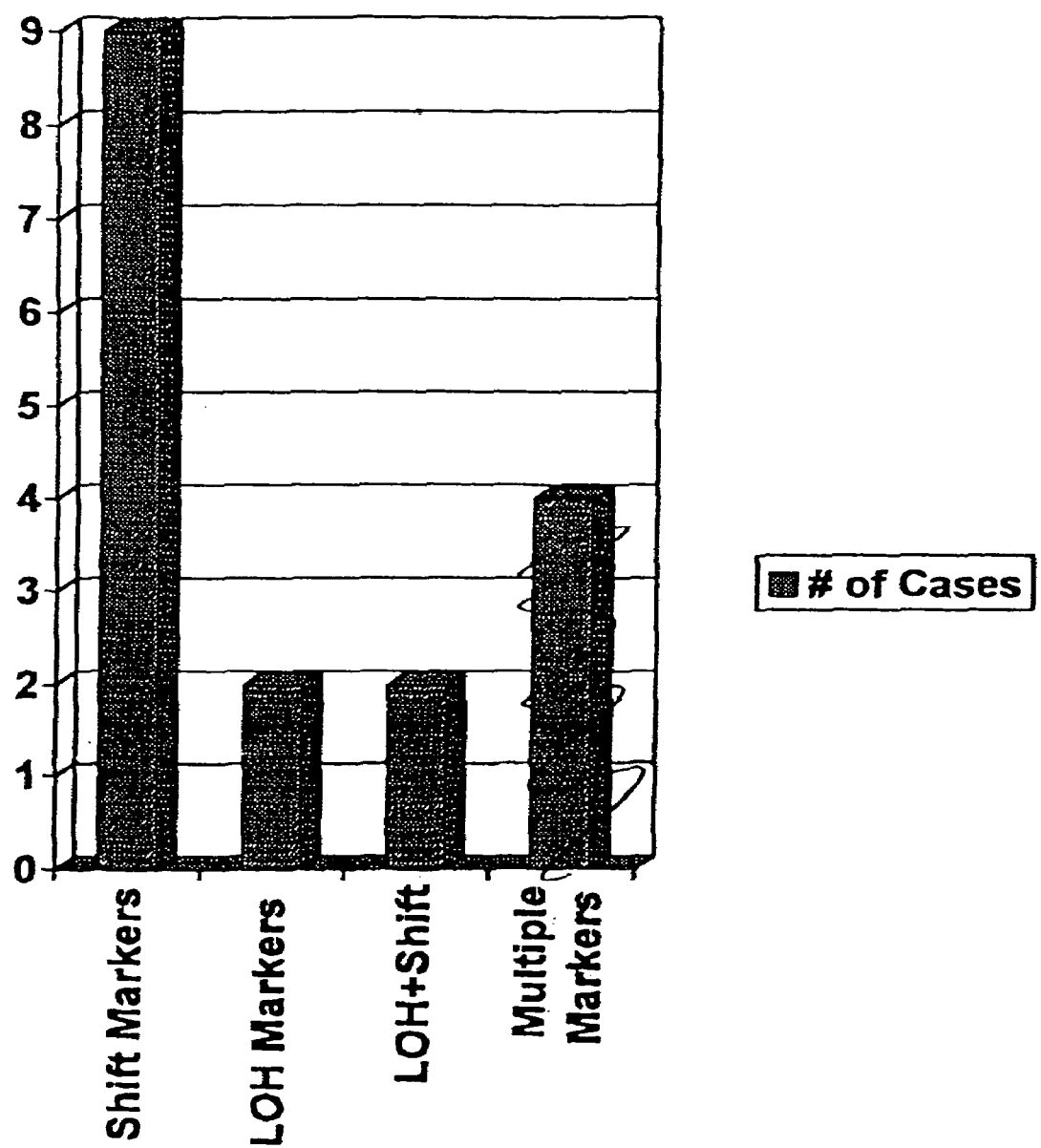
FIG. 3 shows a graph of shifts or LOH at various loci as determined by analysis of saliva samples.

FIGS. 1-3 show the results of analysis of saliva from patients and the identification of mutations in nucleic acid obtained from saliva specimens. The identification of mutations in the nucleic acid correlated with the identification of a tumor of the head and neck or lung in the patients.

The foregoing is meant to illustrate, but not to limit, the scope of the invention. Indeed, those of ordinary skill in the art can readily envision and produce further embodiments, based on the teachings herein, without undue experimentation:

---

The invention claimed is:

1. A method for indicating the presence or risk of a head and neck or lung cancer in a subject, comprising:
isolating nucleic acid from a saliva specimen taken from a subject,
amplifying a nucleic acid using a panel of amplification primer pairs that hybridize to a flanking region of target mutant microsatellite nucleotide sequence in the nucleic acid, wherein the panel comprises the primer pair of SEQ ID NOs:73 and 74 or the primer pair of SEQ ID NOs:77 and 78, thereby generating amplification products, and
detecting the target mutant microsatellite nucleotide sequences in the amplification products, wherein the presence of the mutation is indicative of the presence or risk of a head and neck or lung cancer in the subject.

2. The method of claim 1, wherein the panel further comprises additional primers selected from the group consisting of SEQ ID NOS:33 to 166.

3. The method of claim 1, wherein the primer pairs comprise a detectable label, and wherein detecting a target mutant microsatellite nucleotide sequence comprises detecting the detectable label.

4. The method of claim 3, wherein the detectable label comprises biotin, avidin, streptavidin, an enzymatic label, a fluorescent label, a chemiluminescent label, or a radionuclide label.

5. The method of claim 1, further comprising contacting the amplification products with an oligonucleotide probe that hybridizes to a target mutant microsatellite nucleotide sequence, and wherein detecting a target mutant microsatellite nucleotide sequence comprises detecting hybridization of the oligonucleotide probe to the target mutant nucleotide sequence.

6. The method of claim 5, wherein the oligonucleotide probe comprises a detectable label, and wherein detecting hybridization comprises detecting the detectable label.

7. The method of claim 6, wherein the detectable label comprises biotin, avidin, streptavidin, an enzymatic label, a fluorescent label, or a radionuclide label.

8. The method of claim 1, wherein the target mutant microsatellite nucleotide sequence is flanked by SEQ ID NO:162 or 171.

9. The method of claim 1, wherein the primer pair of SEQ ID NO:73 and 74 generates an amplification product, wherein the amplification product is D9S162.

10. The method of claim 1, wherein the primer pair of SEQ ID NO:77 and 78 generates an amplification product, wherein the amplification product is D9S171.

* * * * *